(12) United States Patent
Ninni et al.

(10) Patent No.: US 12,156,704 B2
(45) Date of Patent: Dec. 3, 2024

(54) INTRALUMINAL NAVIGATION USING GHOST INSTRUMENT INFORMATION

(71) Applicant: CANON U.S.A., INC., Melville, NY (US)

(72) Inventors: Brian Ninni, Woburn, MA (US); HuaLei Shelley Zhang, Brookline, MA (US)

(73) Assignee: Canon U.S.A., Inc., Melville, NY (US)

(*) Notice: Subject to any disclaimer, the term of this patent is extended or adjusted under 35 U.S.C. 154(b) by 23 days.

(21) Appl. No.: 17/553,149

(22) Filed: Dec. 16, 2021

(65) Prior Publication Data

US 2022/0202500 A1 Jun. 30, 2022

Related U.S. Application Data

(60) Provisional application No. 63/132,070, filed on Dec. 30, 2020.

(51) Int. Cl.
*A61B 1/00* (2006.01)
*A61B 1/018* (2006.01)
*A61B 34/00* (2016.01)
*A61B 34/20* (2016.01)
*G06T 11/00* (2006.01)

(52) U.S. Cl.
CPC .......... *A61B 34/20* (2016.02); *A61B 1/0005* (2013.01); *A61B 1/00135* (2013.01);
(Continued)

(58) Field of Classification Search
CPC ....... A61B 34/20; A61B 34/25; A61B 1/0005; A61B 1/00135; A61B 1/00149;
(Continued)

(56) References Cited

U.S. PATENT DOCUMENTS

| 8,583,274 | B2 | 11/2013 | Mohr et al. |
| 10,390,890 | B2 | 7/2019 | Jagga |
| 2007/0018975 | A1* | 1/2007 | Chuanggui ............ A61B 34/20 345/419 |
| 2008/0004603 | A1 | 1/2008 | Larkin et al. |

(Continued)

FOREIGN PATENT DOCUMENTS

| JP | 2013537444 A | 10/2013 |
| JP | 2015514492 A | 5/2015 |
| JP | 2020536657 A | 12/2020 |

OTHER PUBLICATIONS

Scholz, M. et al., "Development of an Endoscopic Navigation System Based on Digital Image Processing, "Computer Aided Surgery, 1998, pp. 134-143, vol. 3, No. 3.

*Primary Examiner* — Timothy J Neal
*Assistant Examiner* — James Edward Boice
(74) *Attorney, Agent, or Firm* — Canon U.S.A., Inc. IP Division

(57) ABSTRACT

A robot-assisted endoscope system and control methods thereof allow a user to perform intraluminal interventional procedures using a steerable sheath. A processor generates a ghost image based on a non-real-time insertion trajectory of the sheath, and a real-time image based on a real-time insertion trajectory for inserting an interventional tool through the sheath towards the target site. A display screen outputs navigation guidance data for informing a user how to manipulate the distal section of the sheath towards the target site such that the real-time image overlaps or coincides with at least part the ghost image and the real-time insertion trajectory becomes aligned with the non-real-time insertion trajectory.

21 Claims, 10 Drawing Sheets

(52) U.S. Cl.
CPC .......... *A61B 1/00149* (2013.01); *A61B 1/018* (2013.01); *A61B 34/25* (2016.02); *G06T 11/00* (2013.01); *A61B 2034/2057* (2016.02); *A61B 2034/2065* (2016.02); *A61B 2034/252* (2016.02); *A61B 2034/254* (2016.02); *G06T 2210/41* (2013.01)

(58) Field of Classification Search
CPC ............ A61B 1/018; A61B 2034/2057; A61B 2034/2065; A61B 2034/252; A61B 2034/254; A61B 2034/2051; A61B 34/30; G06T 11/00; G06T 2210/41
USPC .................................................. 600/121, 114
See application file for complete search history.

(56) References Cited

U.S. PATENT DOCUMENTS

| | | | |
|---|---|---|---|
| 2009/0171371 A1 | 7/2009 | Nixon et al. | |
| 2012/0289777 A1* | 11/2012 | Chopra | A61B 1/00055 382/128 |
| 2014/0176661 A1* | 6/2014 | Smurro | G16H 20/40 348/14.06 |
| 2015/0223668 A1 | 8/2015 | Gilboa et al. | |
| 2016/0029880 A1* | 2/2016 | Kumar | A61B 1/015 600/156 |
| 2017/0325896 A1* | 11/2017 | Donhowe | G16H 40/63 |
| 2018/0036084 A1 | 2/2018 | Krimsky | |
| 2018/0360310 A1* | 12/2018 | Berlin | A61B 3/14 |
| 2019/0167370 A1 | 6/2019 | Olson | |
| 2019/0321107 A1 | 10/2019 | State et al. | |
| 2020/0078103 A1* | 3/2020 | Duindam | A61B 1/00097 |
| 2020/0331147 A1 | 10/2020 | Larkin et al. | |

\* cited by examiner

Step 1

Step 2

INTRALUMINAL NAVIGATION USING GHOST INSTRUMENT INFORMATION

CROSS-REFERENCE TO RELATED APPLICATIONS

The present application claims priority to U.S. provisional applications No. 63/132,070 filed Dec. 30, 2020, the disclosure of which is hereby incorporated by reference in their entirety for all purposes. Priority benefit is claimed under 35 U.S.C. § 119(e).

BACKGROUND INFORMATION

Field of Disclosure

The present disclosure generally relates to medical devices. More particularly the disclosure relates to systems and methods for robot-assisted medical devices configured to navigate one or more tools into a bodily lumen.

Description of Related Art

Robot-assisted minimally invasive surgery (MIS) is known across several surgical domains. Robot-assisted MIS procedures use an endoscope or catheter instrument to inspect, resect, ablate cauterize, staple, seal, or otherwise diagnose and treat delicate organs or tissue of a patient with great precision. Nevertheless, a physician must take great care to minimize patient discomfort while performing these delicate medical procedures. To that end, a physician may use pre-operative and/or intra-operative imaging techniques, such as Computed Tomography (CT), Magnetic Resonance Imaging (MRI), ultrasound (US), or other similar techniques to safely guide surgical tools through or around internal structures and organs of a patient. However, even with image-guided techniques and robot-assisted technology, there is a possibility of inadvertent damage to delicate organs during these procedures.

In the current state of the art, robotically controlled endoscope systems deploy an imaging device (e.g., a fiber-based probe or a miniaturized camera) through a tool channel of a protective sleeve or sheath (also referred to as a catheter sheath or catheter) to first obtain an image of a target site. Then, the imaging device is removed, and a surgical tool is inserted through the tool channel to complete a procedure. A handheld controller (e.g. a gamepad controller) can serve as an interface between the physician and the robotic system to control endoscope navigation within the body of a patient. A display device, such as a liquid crystal display (LDC) monitor provided in a system console or attached to a wall, displays an image of the endoscope's field of view (endoscope image) to assist the user in navigating the endoscope through the patient's anatomy to reach a target site inside the patient. In this process, the orientation of the imaging device, the orientation of the gamepad controller, and the orientation of the endoscope tip are typically mapped to each other before inserting any surgical tool into the patient's anatomy. Currently, there are numerous catheters on the market with embedded position sensors and/or shape sensors, e.g., electro-magnetic (EM) sensors, which allow for tracking of the catheter during the procedure. When combined with patient pre-operative imaging, image segmentation, and intra-operative device-to-image registration, the physician can visualize a virtual representation of the patient's organs and the catheter position throughout the procedure.

Some catheters use removable cameras, meaning that at some point during the procedure after the camera is removed and a surgical instrument is inserted, the virtual representation is the only resource the user has to identify the catheter location within the patient's anatomy. In this case, the user can rely on the EM tracking to finish the procedure after the camera has been removed. For example, to take a biopsy sample of an organ, the physician navigates the endoscope to the target site and aligns the tip of catheter sheath using a live view image from the camera. Then, after the camera has been swapped for a biopsy tool, the user will rely on EM tracking and/or some type of intra-operative imaging guidance (e.g., fluoroscopy) to complete the procedure. Examples of these processes are described in patent and non-patent publications including, but not limited to, U.S. Pat. No. 8,583,274, US 2015/0223668, US 2020/0331147, and M. Scholz, et al., "*Development of an Endoscopic Navigation System Based on Digital Image Processing*," published by Computer Aided Surgery 3:3, 134-143, in 1998. These previous publications mainly describe the process of displaying a virtual position of a tool (a "ghost" tool) to show the user an estimated real-time position of the tool for completing a procedure.

However, there is a possibility that the tool exchange process can cause he catheter sheath to deviate from the original position. Although the real-time EM position can still assist the clinician in aligning the catheter trajectory with the lesion, the clinician has no way of determining if the position is as ideal as it was when the catheter tip was first aligned using the camera. In particular, for robot-assisted endoscopes, the shape of the catheter sheath will change due to the change in stiffness between the camera and the surgical tool. This change in shape of the catheter sheath will affect both the position and orientation of the tip thereof. Therefore, there is a need for an improved endoscope system which can provide accurate endoscope navigation using the actual non-real-time (initial) instrument information.

SUMMARY OF EXEMPLARY EMBODIMENTS

According to at least one embodiment of the present disclosure, an endoscope system comprises a steerable sheath having a tool channel extending from a proximal end to a distal end of the sheath; an actuator mechanically connected to the proximal end of the sheath; and a processor configured to execute specifically designed software commands to control the catheter device and output navigation guidance data to user interface display.

According to an aspect of this disclosure, a robot-assisted endoscope system has a steerable sheath configured to guide an imaging device and/or a surgical tool through a tool channel thereof. An actuator unit (kinematic actuator) provides an actuating force to the steerable sheath, so as to align the distal end of the sheath with a target site. One or more sensors arranged along the sheath detect a real-time position of the sheath in relation to the target site. A processor generates a virtual image of the real-time position of the sheath and/or the target site, and displays a ghost (non-real-time) position for a tool in the virtual image. Information directing a user to align the distal end of the sheath with the ghost position is displayed on a display screen. The ghost position can be a true prior position that was recorded, or a proposed desired position based on a procedure plan. The appearance of the ghost position is different from the real-time position but aimed to align.

According to another aspect of the present disclosure, an endoscope system, comprises: a steerable sheath having a distal end for insertion into a body and a proximal end for manipulation from outside the body, the steerable sheath having a tool channel extending from the proximal end to the distal end; a sensor arranged on the steerable sheath so at to map a positional relation between the steerable sheath and a target site for treatment; an actuator configured to drive the steerable sheath such that at least part of the sheath moves with respect to the target site; and a processor in data communication with one or more of the actuator and the sensor. The processor is configured to instruct the actuator and acquire the sensor feedback.

According to other embodiments, the processor displays a 'ghost' (non-real-time) position of the steerable sheath in a virtual image; the ghost image can be on or more of a true prior recorded position, or a proposed or desired position based on a procedure plan, or a still image of a virtual tool; the appearance of the ghost image is different from a real-time position image so that a user can visually distinguish the ghost image from the real-time position image when both images are displayed simultaneously; the ghost image and the real-time position image are different in one or more of the following: the annotation, size, shape, color, or opacity of the ghost image as compared to the real-time position image. As used herein, the term "position" comprises both location and orientation information.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

One or more objectives, features, and/or advantages of the present disclosure will become apparent from the detailed description when taken in conjunction with the accompanying figures showing illustrative embodiments of the present disclosure.

DETAILED DESCRIPTION OF EXEMPLARY EMBODIMENTS

Figure 1:
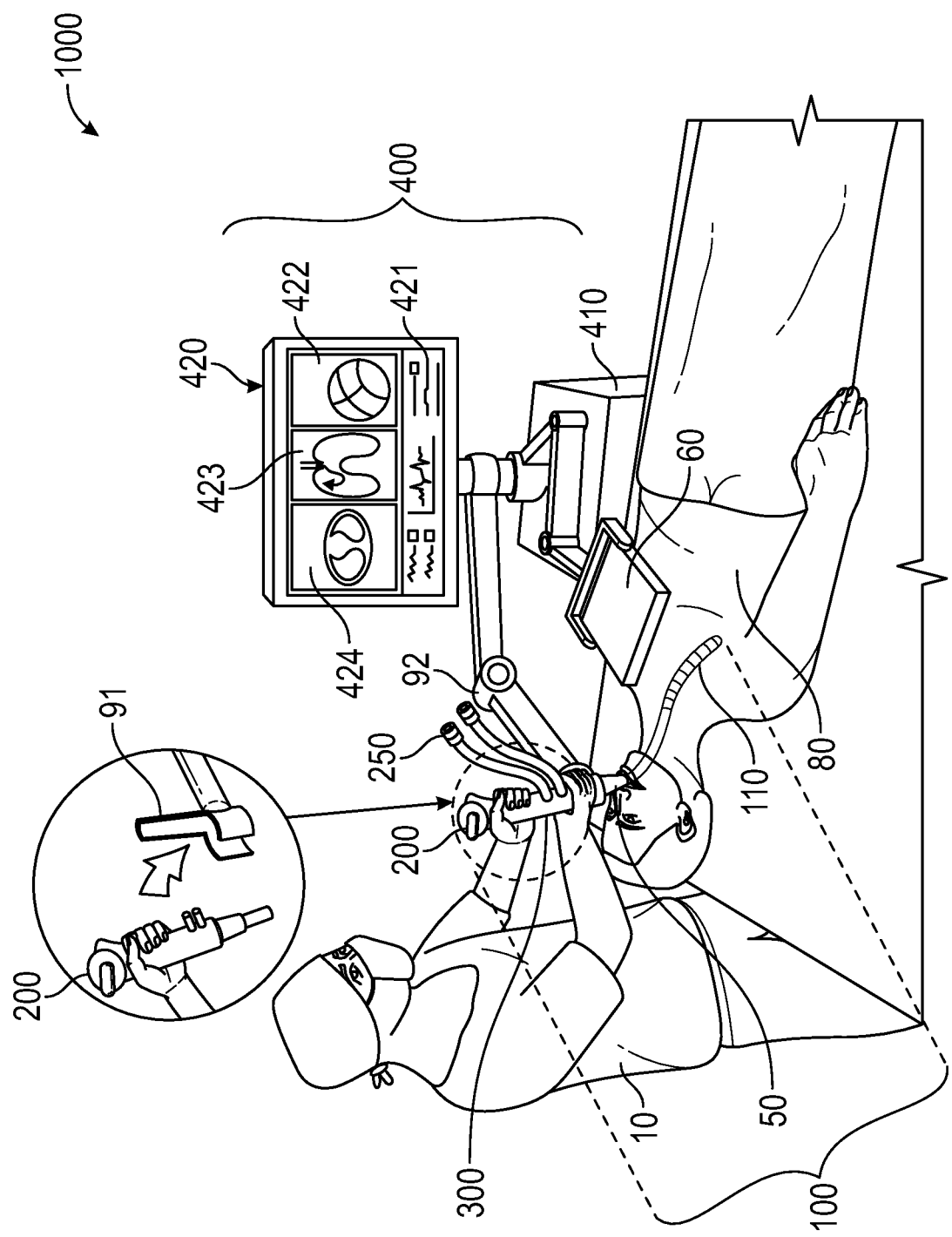
FIG. 1 illustrates an example embodiment of a robot-assisted endoscope system 1000 in medical environment, such as an operating room.

The exemplary embodiments disclosed herein are based on an objective of providing an improved endoscope system which can facilitate a targeting phase of an interventional procedure.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the actions and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade polymer material and having an optical imaging function. A particular example of an optical catheter is a fiber optic catheter which comprises a flexible sheath, a coil, and an optical probe or imaging core contained within the coil. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes. Embodiments of the present disclosure can be applicable to one or more of the foregoing endoscopes.

<Robot-Assisted Endoscope System>

An exemplary configuration of a robot-assisted endoscope system 1000 is described with reference to FIG. 1 and FIG. 2A-2C. FIG. 1 illustrates an example representation of a medical environment such as an operating room where a robot-assisted endoscope system 1000 can be practiced. The robot-assisted endoscope system 1000 may include a steerable instrument 100 (a steerable medical device) operable by a user 10 (e.g., a physician) to perform an endoscopy procedure on a patient 80. The robot-assisted endoscope system 1000 may include a computer system 400 operatively attached to the steerable instrument 100 via a robotic platform 90. The computer system 400 (e.g., a system console) includes a processor or central processing unit (CPU) 410 and a display screen 420 such as a liquid crystal display (LCD), OLED or QLED display. A storage memory 411 (ROM and RAM memory), a system interface 412 (FPGA card), and a user interface 413 (e.g. mouse and keyboard) are operatively connected to the processor or CPU 410 and to the display screen 420.

The steerable instrument 100 includes a handle 200 and a steerable sheath 110, which are removably connected to each other by a connector assembly 50. The handle 200 includes an actuator system 300 which receives electronic commands from computer system 400 to mechanically actuate the steerable sheath 110. The handle 200 is configured to be detachably mounted on the robotic platform 90. The robotic platform 190 includes a robotic arm 92 and a stage 91 for robotically guiding the steerable sheath 110 towards a target site within the subject or patient 80. When the handle 200 is not mounted on the robotic platform 90, the handle 200 can be operated manually by the user 10 to control the steerable sheath 110. For treating or examining the patient 80, the steerable instrument 100 may include one or more access ports 250 arranged on or around the handle 200. Access ports 250 can be used for inserting end effectors or for passing fluids to/from the patient. An electromagnetic (EM) field generator 60 interacts with one or more EM sensors 190 arranged on the steerable sheath 110 for tracking the position, shape, and/or orientation of the steerable sheath 110 while being inserted through a bodily lumen 81 towards a target site 82 within the patient 80.

During an endoscope procedure, the system processor or CPU 410 of computer system 400 is configured to perform operations based on computer-executable code pre-stored in the system's memory 411. The display screen 420 may include a graphical user interface (GUI) configured to display one or more of patient information 421, an endoscope live-image 422, an intra-operative image 423 (e.g., fluoroscopy), and a pre-operative image 424 (e.g., a slice image) of the patient 80.

Figure 2A:
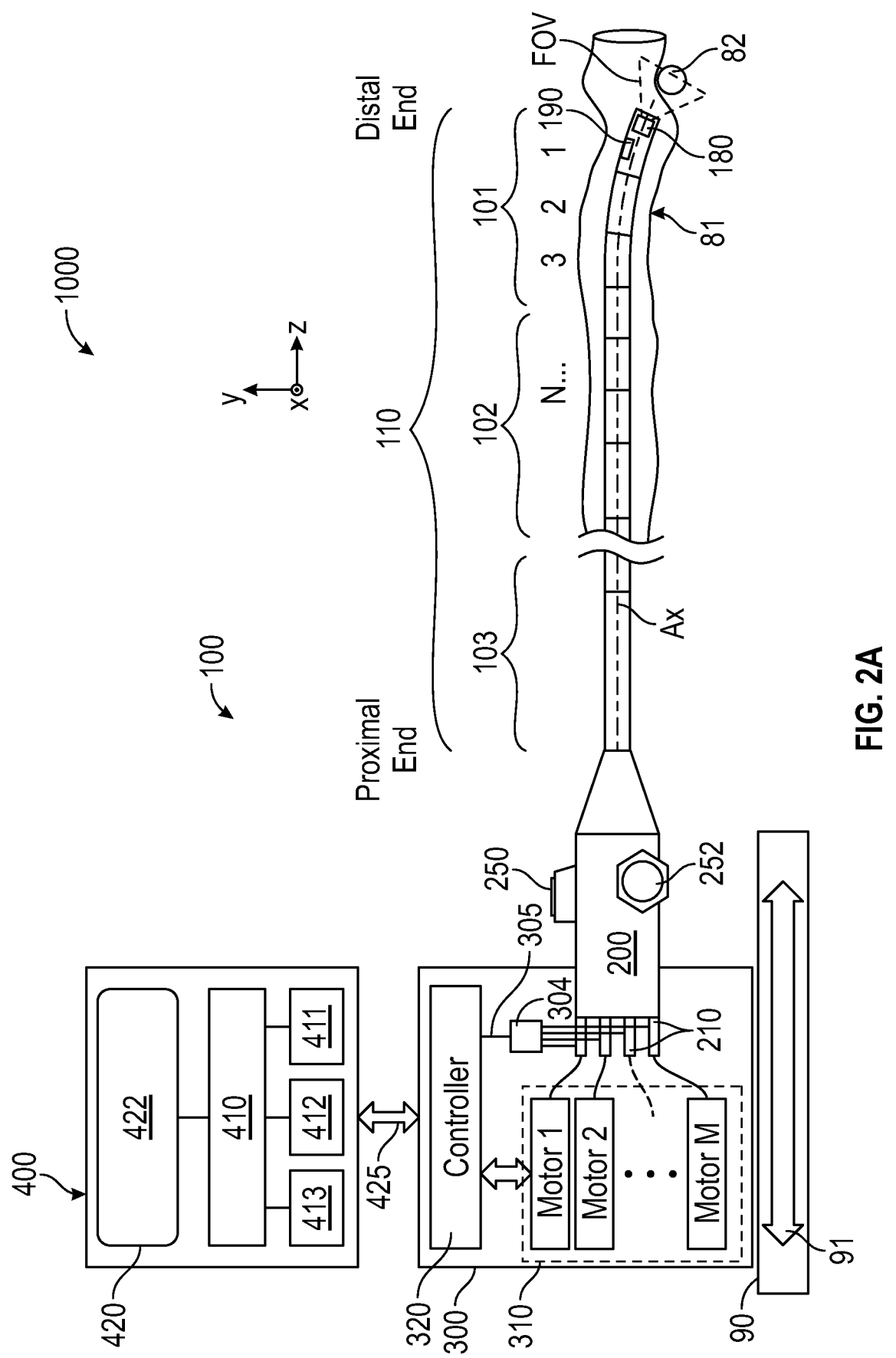
FIG. 2A illustrates an example embodiment of a robot-assisted endoscope system 1000 represented in functional block diagram.

FIG. 2A illustrates a general structure of the robot-assisted endoscope system 1000 in functional block diagram without the user and/or patient. As shown in FIG. 2A, the robot-assisted endoscope system 1000 includes a computer system 400 (e.g. a system console), a robotic actuator system 300, and a steerable instrument 100 which is connected to the actuator system 300 via a handle 200. The steerable instrument 100 includes steerable sheath 110 comprised of a proximal section 103, a middle section 102, and a distal section 101 arranged in this order along a longitudinal axis (Ax). The proximal section 103 is a non-steerable section and serves to connect the steerable section to handle 200 and the actuation system. The middle section 102 and the distal section 101 constitute a steerable section of the steerable sheath and are configured to be inserted into a bodily lumen 81 of a patient 80. The steerable distal section 101 (and middle section 102) are divided into multiple bending segments 1, 2, 3 . . . N which are configured to be bent, curved, twisted, and/or rotated when advancing the steerable sheath through intraluminal tortuous paths of a bodily lumen. Each bending segment includes at least one ring-shaped component. By convention, the steerable instrument 100 operates in a three-dimensional (3D) space defined by a 3D coordinate system of x, y, z Cartesian coordinates. The steerable sheath 110 defines at least one tool channel 105 which extends from the proximal end to the distal end along the longitudinal axis Ax. The steerable sheath 110 may include one or more position and/or orientation sensors 190 arranged on the wall the catheter sheath, and may include a removable imaging device 180, such as a fiber camera or a miniature electronic CMOS sensor arranged in the tool channel 105. The imaging device 180 is arranged such that its imaging plane is in the x-y plane, and the longitudinal axis Ax of the steerable sheath 110 extends along the z-axis of the coordinate system.

For inserting an endoscope into a biological lumen 81 such as an airway of a patient 80, the tip (distal end) of the steerable sheath 110 is advanced (navigated) along a center line of the lumen. In this case, an imaging device 180 (e.g., a miniature camera) can be arranged in the tool channel 105 to provide a live-view image of the lumen 81 taken directly from the instrument's field of view (FOV). However, in some embodiments, the steerable sheath 110 may not allow for the arrangement of a camera within the tool channel. In this case, navigation may be provided by intra-procedural guided imaging based on position and/or orientation provided by the one or more sensors 190 arranged along the sheath. In any case, in order to reach a desired target site 82, the steerable sheath 110 must bend, twist and/or rotate in different directions such that the distal section of the steerable sheath continuously changes shape and direction until it reaches an optimal location aligned with target site 82 such as a tumor.

The bending, twisting, and/or rotation (steering) of steerable sheath 110 is controlled by an actuation system comprised of the handle 200, the actuator system 300 and/or the computer system 400. The actuator system 300 includes a micro-controller 320 and an actuator unit 310 which are operatively connected to the computer system 400 via a network connection 425. The computer system 400 includes suitable software, firmware, and peripheral hardware operated by the processor or CPU 410. The computer system 400, the actuator system 300, and the handle 200 are operably connected to each other by the network connection 425 (e.g., a cable bundle or wireless link). In addition, the computer system 400, the actuator system 300 and the handle 200 are operatively connected to each other by the robot platform 90, which may include one or more robotic arms 92 and translation stage 91. In some embodiments, the actuator system 300 may include or be connected to a handheld controller, such as a gamepad controller or a portable computing device like a smart phone or a tablet. Among other functions, the computer system 400 and actuator system 300 can provide a surgeon or other operator with a graphical user interface (GUI) and patient information shown in the display screen 420 to operate the steerable instrument 100 according to its application.

Figure 2B:
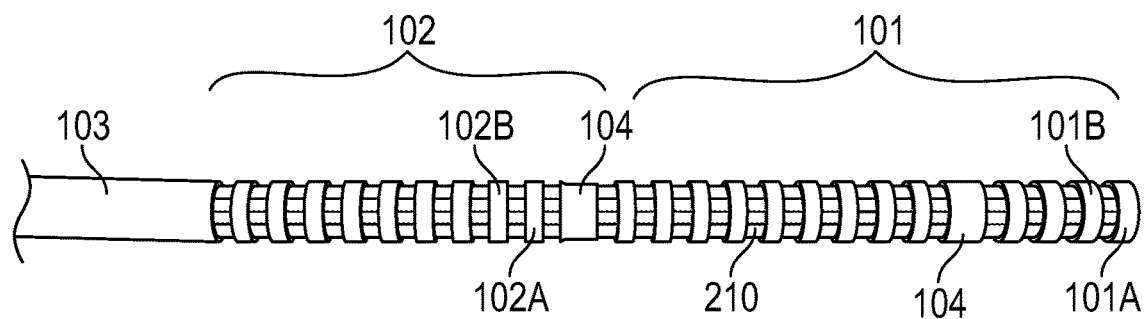
FIG. 2B illustrates an example embodiment of a multi-segment steerable sheath 110.

FIG. 2B shows an example embodiment of steerable sheath 110 which is configured to be removably attached to the handle 200. The bending segments of the steerable sheath 110 may be formed by ring-shaped components (ring 101A, ring 101B, etc.) arranged in the distal section 101, and ring-shaped components (ring 102A, ring 102B, etc.) arranged in the middle section 102. These ring-shaped components include a central opening which forms the tool channel 105, and plural conduits 106 (groves, channels, or thru-holes) arranged lengthwise around the central opening along the wall of each ring-shaped component. The non-steerable proximal section 103 is made of an extruded tubular sheath having the same central opening or tool channel 105, and plural conduits 106 surrounding the central opening. In this manner, at least one tool channel 105 inside the tubular sheath 110 provides passage for endoscope optics and/or other various interventional tools. Endoscope optics may include illumination optics and detection optics; the illumination optics emits illumination light to irradiate an area of interest or target site 82, and the detection optics collects light reflected and/or scattered from the area of interest to form an image. The target site 82 or area of interest can be located along a bodily lumen 81 of the patient 80.

Figure 2C:
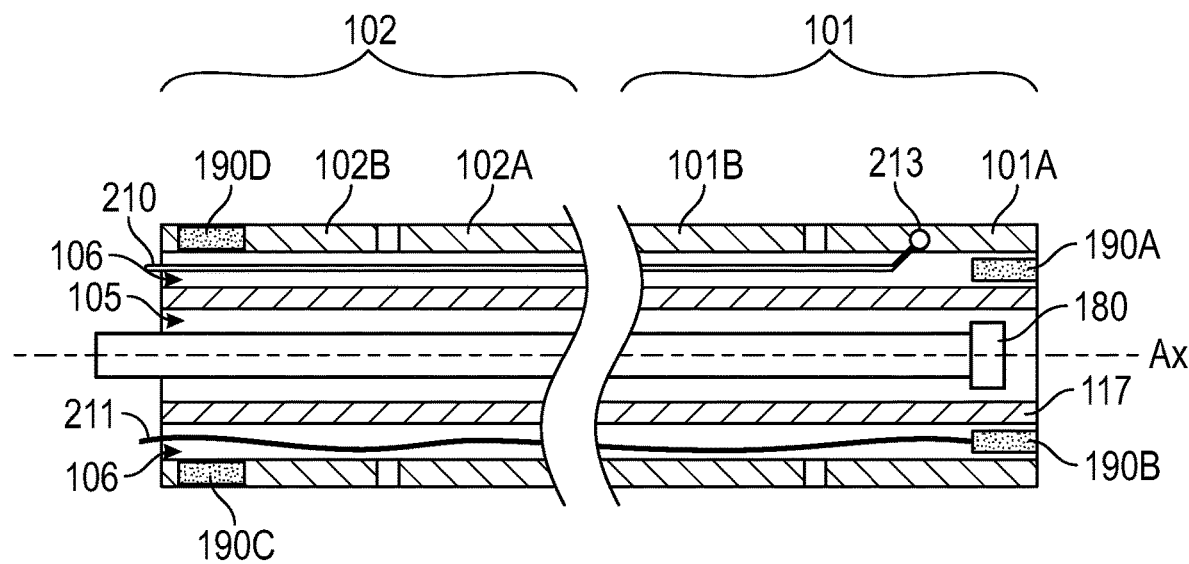
FIG. 2C illustrates a cross-sectional view of the steerable sheath 110 showing, EM sensors 190, a tool channel 105, and wire conduits 106.

FIG. 2C illustrates a cross-sectional sagittal view of the steerable sheath 110 taken along the lengthwise direction of the sheath. Along its length, the steerable sheath 110 includes one or more EM sensors 190, a tool channel 105, and wire conduits 106. An inner sheath 117 is provided to facilitate passage of interventional surgical tools (end effectors) through the tool channel 105 without getting stuck inside the sheath. The distal section 101 of the steerable sheath 110 may contain at the distal end thereof, among other things, one or more sensors 190 fixedly attached to the wall of the sheath 110. In the embodiment shown in FIG. 2C, the distal section 101 includes a first sensor 190A and a second sensor 190B arranged inside wire conduits 106 in the wall of the ring-shaped components (e.g., ring 101A) at the distal end of the sheath 110. One or more additional sensors can be arranged at any other convenient location of the sheath. For example, as shown in FIG. 2B, the steerable section includes the distal section 101 formed by a plurality of ring-shaped components (rings 101A, 101B, etc.) and the middle section 102 formed by plurality of ring-shaped components (rings 102A, 102B, etc.). The steerable section is bendable in one or more directions at inflection points 104 by an actuation force (push or pull force) applied to one or more drive wires 210. Therefore, the one or more additional sensors can be provided in the middle section 102 and/or at the inflection points 104 to track the location and shape of the sheath 110 during navigation. In FIG. 2C, two additional sensors 190C and 190D are provided in the middle section 102 on the outer surface of ring 102B. As long as the sensors 190 can provide accurate information to map a posture and/or positional relation between the steerable sheath 110 and the target site 82, the arrangement of these sensors is not limited to any specific location or type of sensor.

In one embodiment, the sensors 190 are part of an EM sensor system configured to map the operation of the robotic controller 320 (e.g., a gamepad controller or handle 200) with the shape, position, and/or orientation of the steerable catheter sheath 110. For example, a plurality of EM tracking sensors each with 6 Degrees of Freedom (6DOF) can be used to detect and estimate an amount of the twist, bend, and/or rotation of the middle and distal sections of the catheter sheath independently from each other. One or more sensors (e.g., a first sensor 190A and a second sensor 190B) detect and track the position and orientation of the sheath's distal tip with respect to the target site. One or more additional sensors 190C and 190D may detect and track any changes in shape (bending) or deformation (ovalization) of the middle section of the sheath. A typical 6DOF EM sensor with a sub-millimeter diameter and about 5 mm length can measure both position and orientation. Therefore, a first pair of EM sensors (e.g., sensor 190A and sensor 190B) can measure position and rotation of the distal end of the sheath with respect to the target site, and an additional EM sensor 190C can measure the movement (bend, twist, rotation, etc.) of the middle section of the catheter sheath 110. In this manner, the signals of these EM sensors can be used by the controller 320 or system processor or CPU 410 to accurately track any changes in shape, position, and/or orientation of the various sections of catheter sheath body, and of the distal end of the sheath independently from each other. The controller 320 can control each control wire 210 by actively driving an actuator or motor (310), sensing a sensor (304 or 190), and operating according a feedback signal 305 to implement appropriate shaft guidance for navigating through tortuous intraluminal paths of the patient's anatomy.

Control wires 210 are passed through one or more of wire conduits 106 along the wall of the ring-shaped components. The distal end of control wires 210 are fixedly attached to the sheath at various points along the steerable section. For example, in FIG. 2C, a control wire 210 is attached to the most distal ring 101A at an anchoring point 213. Other control wires 210 are attached in a similar manner to inflection points 104. The wire conduits 106 also serve to pass therethrough other types of wires. For example, as shown in FIG. 2C, the conduits 106 serve to pass electrical cables 211 used to connect sensors 190 to the actuator system or computer system.

Referring back to FIG. 2A, the handle 200 provides an electromechanical interface between the steerable instrument 100 and the robotic actuator system 300 and/or the robotic platform 90. For example the handle 200 may provide an interface for mechanical, electrical, and/or optical connections, and a data/digital connection for interfacing the steerable sheath 110 with the actuator system 300 and/or computer system 400. The handle 200 may also provide one or more input ports 250 that a surgeon or operator can use to insert end effector tools through the tool channel 105. The handle 200 may also include one or more dials 252 for manual steering of the steerable section 101 of the sheath 110. The term "end effector" refers to a working part of a surgical tool. Endoscopic surgical tools may include clamps, graspers, scissors, staplers, ablation needles, and other similar tools, which serve to manipulate body parts (organs or tumorous tissue) during examination or surgery, as it is known to those of ordinary skill in the art.

The robotic actuator system 300 includes an actuator unit 310 and a microcontroller 320. The actuator unit 310 may include a plurality of actuating motors (or actuators), which are shown as Motor 1 through Motor M, where M is an integer greater than one and equal to a number of control wires 210 necessary for steering the various segments of the steerable sheath 110. The control wires 210 are anchored at various points along the steerable section of the sheath 110. The robotic actuator system 300 also includes one or more sensors 304. Sensors 304 can include a strain sensor and/or a displacement sensor (e.g., a Hall-effect sensor) which serve to detect and/or measure compressive or tensile forces exerted by a push or pull force applied by the actuator unit to the control wires 210. The sensors 304 can output a feedback signal 305 corresponding to the amount of compressive or tensile force (an amount of strain) being applied to each control wire 210 while operating (steering) the steerable sheath 110. The signals 305 from the sensors 304 for each control wire 210 are fed into the microcontroller 320 to control each actuator or motor individually. In this manner, each control wire 210 can be actively controlled to implement appropriate shaft guidance for navigating the steerable sheath 110 through intraluminal tortuous paths of a patient's anatomy.

In one example, when using a shaft guidance system, the steerable sheath 110 is robotically advanced through a lumen 81 while sensors (304 and/or 190) measure the insertion depth of the catheter tip and the angulations of the steerable sections to obtain insertion trajectory information. The trajectory information is stored in a memory of the system and continuously updated. After a short advance in insertion distance, the shape of the steerable sheath is corrected by adjusting (twisting and/or bending) segments of the instrument in such a way that the new shape closely matches the desired trajectory. This process is repeated until a target area is reached. The same process is applied when the steerable instrument is withdrawn from the patient. This is analogous to known navigation techniques, e.g., as described in US 2007/0135803, which is incorporated by reference herein for all purposes.

Referring back to FIG. 1, for a catheter sheath with a removable imaging device (or catheters without an imaging device), the physician must rely on the EM tracking to complete the endoscopy procedure. For example, to take a biopsy sample using the steerable sheath 110, the sheath is navigated to the target site without the biopsy tool in the tool channel. After the sheath is aligned with the target site, if an imaging device (camera) is used for navigation, the camera is removed and swapped with a biopsy tool. However, there is a risk that this tool exchange has caused the catheter to deviate from the original position. In the same manner, even if a camera is not used for the initial insertion of the steerable sheath, the insertion of the biopsy tool may deviate the distal end of the sheath from its original position. Although the real-time EM position could assist the clinician in aligning the catheter trajectory with the target site, the clinician has no way of determining if the position of the target site with respect to the inserted tool is as ideal as it was when distal end of the sheath was originally aligned with the target site. In particular, even if an endoscope imaging device is used for the initial navigation, the shape of the catheter sheath will change due to the change in stiffness between the camera and the biopsy tool. This change in shape will affect both the position and orientation of the catheter tip with respect to the target site.

<Real-Time Tool Realignment Based on Ghost Tool Information>

According to one embodiment, in a case where the distal end of the steerable sheath becomes misaligned with the target site, to realign the distal end of the steerable sheath a solution is to have the software system display a 'ghost' (non-real-time) position of the tool in the virtual image. This ghost position (ghost image) can be a true prior position that was recorded by the system during an initial insertion of the sheath, or a proposed or desired position based on the procedure plan. The appearance of this ghost image needs to be displayed differently from the real-time position of the steerable sheath so the user can distinguish the two when both images are displayed simultaneously. This can be done in various ways, for example by changing the annotation (ID), size, shape, color, or opacity of the ghost image and/or the real-time image.

<Recording Initial Position>

According to one embodiment, the software system (i.e., CPU 410) can allow the user to record the position of the catheter sheath at any point in time during a routine examination process of a bodily lumen. The software system can also be programmed to automatically record the position of suspect objects along a bodily lumen based on certain criteria or scenarios. One use case scenario of recording an initial position would be to mark one or more points of interest (points suspected of diseased tissue) along the path of the sheath while navigating through a bodily lumen to return later to such locations for further inspection. Another use case scenario can be to program the software system to record the position and shape of at least part of the catheter sheath before swapping the imaging device 180 for an interventional tool (e.g., biopsy tool). As previously mentioned above, there is a high possibility that a shape of the catheter sheath will change due to a difference in stiffness between the camera and biopsy tool. Advantageously, however, when the software system is programmed to overlay the recorded position and the real-time position in the virtual view, the user and/or the processor itself can identify how much deviation has occurred due to the tool exchange.

Another embodiment of this function can be applied to a mode change in the steerable sheath. For example, when the user enters a "Targeting Mode", the robot-assisted endoscope system can record the initial position and track the procedure until the targeting mode ends. In "Targeting Mode", the user can control both the distal and middle sections of the steerable sheath until the catheter sheath is aligned with a target site. However, when exiting targeting mode and entering a follow-the-leader (FTL) mode, the shape of the catheter does not closely resemble the initial shape. As a result, it would not be possible to ensure smooth continuous motion during reverse FTL (rFTL), where, when retracting the catheter, the controller commands the shape of the catheter to match the shape it was at the corresponding linear stage position during insertion. According to the present disclosure, one way to re-align back to the initial position is to record the position at the start of Targeting Mode, and, at the end of Targeting Mode, and possibly at other points between the start and end of the targeting mode. Then, the software system can be programmed to direct the user on how to bend the catheter sheath to return the real-time position to the initial (recorded) position along the insertion and/or extraction path.

<Alignment Assistance>

The foregoing examples are just a few scenarios where it can be advantageous to provide a ghost image to realign the steerable sheath of a robot-assisted instrument to a desired or recorded initial position. There are many other scenarios where the user will want to align the real-time catheter position with the ghost position. Another use case scenario is to display an 'ideal' placement of the catheter, for example to take a biopsy sample of a target site. This position could be better aligned with the center of a lesion, or aimed to avoid critical structures in the path to the lesion. In this case, the software system will need to be programmed taking into account a number of parameters of both the catheter and the patient lumen when determining this ideal position.

For example, on one hand, the catheter has to be physically capable of bending to the desired orientation. To determine this, the software system needs to know the stiffness and dimensions of the catheter sheath, as well as the relative angle between bending sections. In addition, the catheter sheath has to be physically capable of moving to the desired position while staying within the constraints of the lumen. To that end, the software system can be programmed to minimize deviation of the sheath from the centerline of the lumen. Moreover, when dealing with delicate target sites (e.g., a brain tumor), the software system needs to maintain the catheter sheath within a certain distance range away from the lesion or surrounding structures. If the tip of the steerable sheath is too close to the target site, the catheter sheath might have to bend at an angle that will make it impossible for a tool to pass through the sheath, or bend an angle that makes is impossible for the tool be aligned with the target site. On the other hand, if the tip of the steerable sheath is too far from the target site, the angle of bending can be limited such that the sheath might need little bending, but the tool may have a risk of deviating from the target due to the longer trajectory it has to travel. Therefore, according to at least one embodiment of the present disclosure, the software system is programmed to iteratively use the ghost position information to provide accurate sheath navigation by updating (manipulating) the position and/or orientation of the sheath until the real-time position matches the ghost position.

Figure 3:
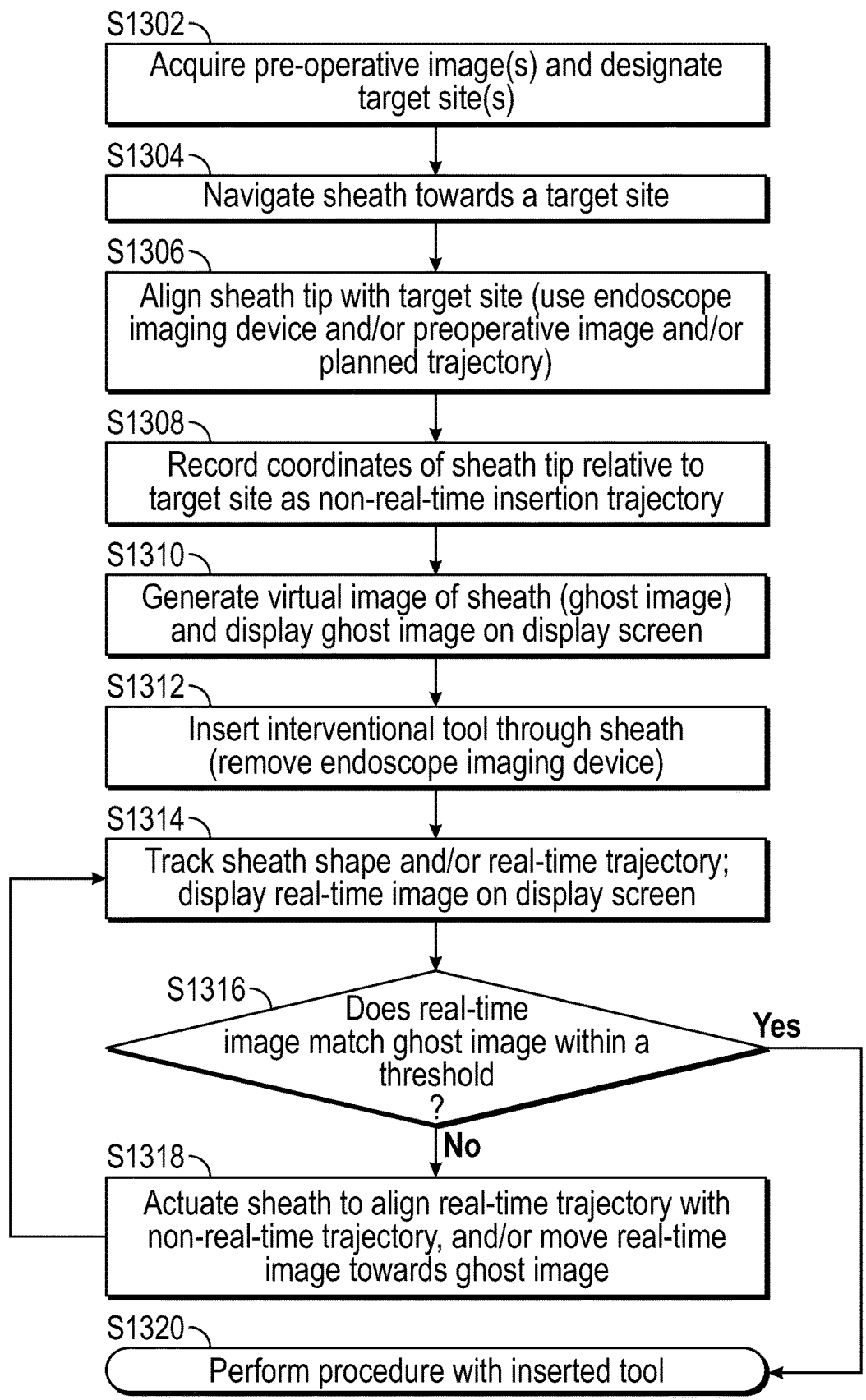
FIG. 3 illustrates a workflow process 1300 for robot-assisted endoscope intraluminal navigation using non-real-time sheath positional information represented by a "ghost image" and real-time sheath positional information represented by a real-time image.

FIG. 3 illustrates an example flow process 1300 according to an embodiment of the present disclosure. FIG. 3 is an example workflow, the user needs to navigate the steerable catheter sheath 110 through a bodily lumen 81 (a vessel or airway) to a target site 82 (suspected lesion) using an imaging device 180 (a removable endoscope camera), save the position of the catheter sheath, exchange the imaging device for an interventional tool, and then to return or realign the catheter sheath to the saved position. The workflow can be broadly outlined as a first step to Navigate the catheter sheath to a lesion and align the catheter sheath to the lesion using a camera; a second step to "notify" the software system that camera will be swapped with a biopsy tool; a third step to cause the software system to record the catheter sheath position and display the sheath position as a "ghost image" in a virtual view of a display screen; a fourth step to prompt a user to swap the camera for a biopsy tool, and track the insertion of the tool in real-time; a fifth step of determining how the real-time position deviates from the recorded "ghost" position; and a sixth step of actuating the sheath to bend the middle and tip sections of the catheter sheath to realign the real-time position with saved position.

The workflow of FIG. 3 is not limited to the above example. More specifically, the workflow process 1300 assumes an active state of the robot-assisted endoscope system 1000 in which the steerable catheter sheath 110 is attached to the handle 200 and mounted in the robot platform 90. In this state, at step S1302, the system processor or CPU 410 of computer system 400 displays the patient information 421, a pre-operative image 424 and/or an intra-operative image 423 on display screen 420 (see FIG. 1). From the displayed images, the physician designates a target site or desired location to where the tip of the catheter sheath will be navigated. At step S1304, the robot-assisted system navigates the steerable sheath 110 through the patient's lumen to the target site. This step S1304 is performed in collaboration with the user's input, and control of the actuator system 300 via the handle 200. At step S1306, the system aligns the tip (distal end) of the catheter sheath with the target site. In this step S1306, the system may use a planned trajectory, the pre-operative image 424, the intra-operative image 423, or the imaging device 180 (e.g. an endoscope camera) to align the distal end of the endoscope with the target site 82. At step S1308, the system processor or CPU 410 records (stores) in memory 411 the position and/or orientation of the sheath's tip in relation to the target site. Here, recording the position and/or orientation of the sheath is not limited to the sheath's tip alone. The position and/or orientation of the sheath can be one or more positions with associated cyclic motion phases correlated with patient biological activity (e.g., respiratory or cardiac cycle depending on applications). Therefore, at step S1308, the "position" can be a series of positions during a cyclic motion cycle (with a motion waveform being recorded) if the camera has a clear view of the trajectory path and/or target during all these positions. Motion includes respiratory or cardiac motions depending on the application. This process is further explained with respect to FIG. 10.

At step S1310, the system processor or CPU 410 generates a virtual image of the sheath 110 (ghost image) using the recorded (desired) location of the distal end of the sheath. At this step S1310, the processor or CPU 410 displays the ghost tool image and related positional information thereof on the display screen 420. At step S1312, the physician is prompted to insert the actual interventional tool (e.g., a biopsy tool) through the steerable sheath 110. In the case where the steerable sheath 110 is equipped with a removable imaging device 180, the user first removes the imaging device 180 from the sheath, and then inserts the actual interventional tool. At step S1314, the system uses the one or more position and/or orientation sensors 190 located along the wall of the sheath to track in real-time the insertion of the interventional tool. In this step S1314, the system displays a real-time representation (a real-time image) of the interventional tool being inserted through the sheath 110. At step S1316, the processor or CPU 410 determines whether the real-time tool position matches the recorded (non-real-time) position of the catheter sheath represented by the ghost image. If the determination at step S1316 is negative (NO at S1316), the flow process advances to step S1318.

At step S1318, the system processor or CPU 410 executes an algorithm to realign the real-time tool tip position with the recorded ghost sheath position. At this step S1318, the processor or CPU 410 may output indications for the user to operate on the GUI of display screen 420 to align the real-time tool image with the recorded non-real-time ghost image. For example, the system processor or CPU 410 can display a distance and angle of the difference between the ghost image and the real-time tool image. Then, the user may manipulate the position and or orientation of the catheter sheath by operating the robotic actuator system 300 via the handle 200. Alternatively, the system can be programmed to accept an interactive input from the user via the GUI at the display screen 420. In this case, the user can move (e.g., drag) the real-time tool image towards the non-real-time ghost image, and the processor or CPU 410 can be programmed to convert the user input into control signals to cause the actuator system 300 to manipulate the sheath 110. These steps S1314-S1316-S1318 can be iteratively repeated until the system and/or the user determines that the real-time tool position matches the recorded ghost position within a predetermined threshold. That is, when the determination at step S1316 is positive (YES at S1316), the flow process proceeds to step S1320. At step S1320, after the system has determined that the interventional tool is accurately aligned with the target site, the system proceeds to complete the procedure (e.g., a biopsy procedure or ablation procedure) with the inserted interventional tool (e.g., a biopsy needle).

According to at least one embodiment, the "ghost image" can be a "moving" image updated according to the motion phase of the patient's biological activity cycle (e.g., a breathing or heartrate cycle). This can be advantageous when navigating an interventional tool through the steerable sheath 110 during in-vivo interventions, so targeting aims to have real-time positional alignment (location & orientation) of the sheath with the planned position and temporal alignment with the motion phase. Therefore, in step S1316, as long as the real-time representation returns to one of the positions at the correct motion phase, it is permitted to target a desired location. The "non-real-time ghost image" can be displayed according to the matching motion phase to allow the real-time catheter position to align both spatially and temporally with the "ghost image".

Figure 4A:
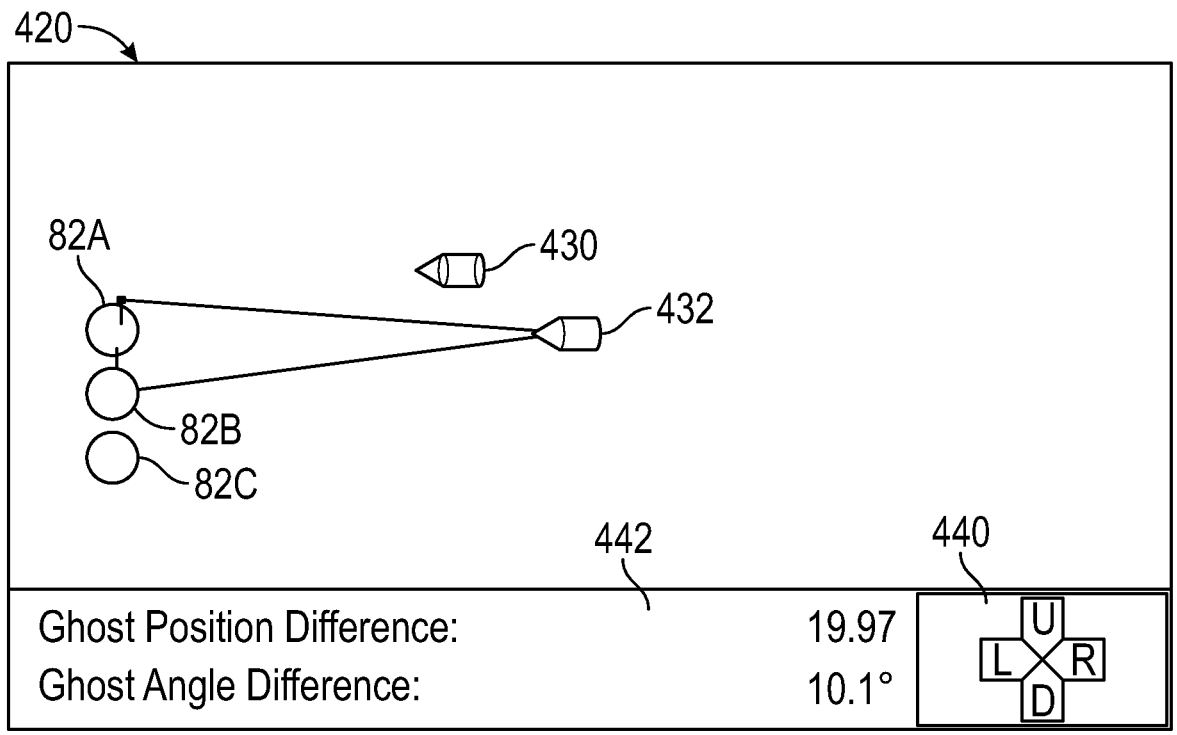
FIG. 4A and FIG. 4B show an example of how the software system can indicate to the user a difference in position and/or orientation between a ghost image 430 and a real-time image 432 with respect to one or more target site(s) 82.
Figure 4B:
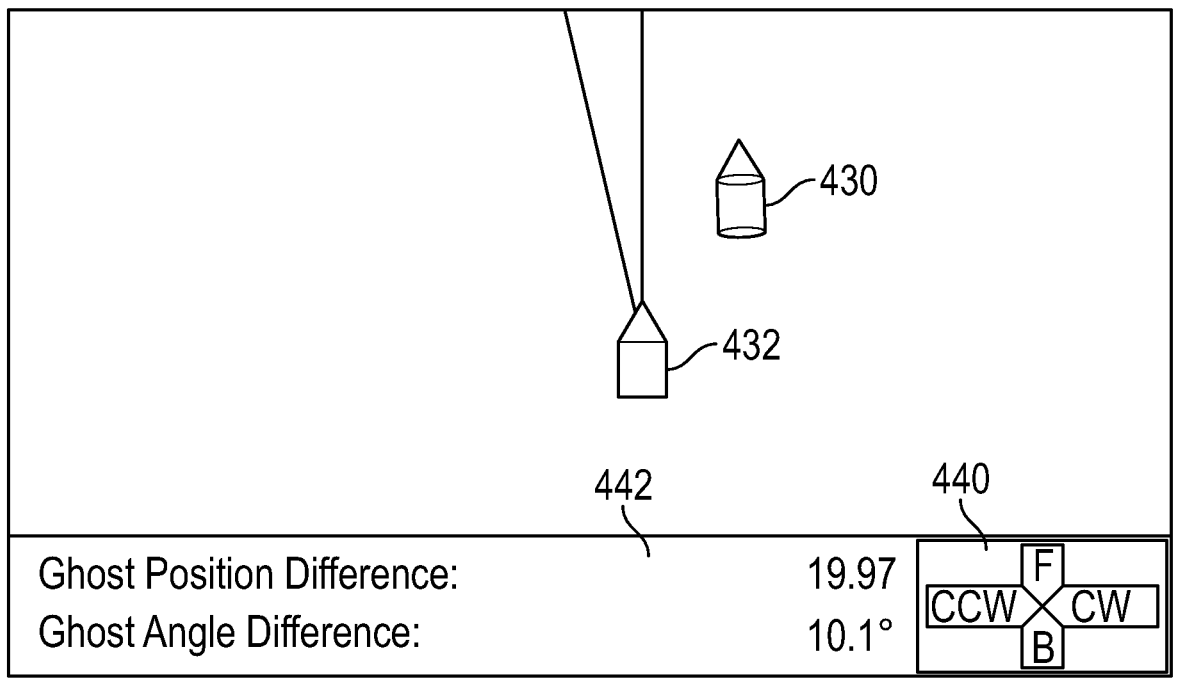

FIG. 4A and FIG. 4B show an example of how the software system can indicate to the user the difference in position and/or orientation between a non-real-time ghost image 430 and a real-time position image 432 with respect to one or more target site(s) 82. FIG. 4A and FIG. 4B shows top and side perspectives, respectively, of ghost image 430 and real time position image 432. As shown in these figures, the software system can display measurements of the differences between the real-time image 432 and the ghost image 430 with respect to a chosen target site. In FIG. 4A, a display section 442 of the display screen 420 shows information about a difference in location and orientation between the real-time image and the ghost image, including: "Ghost Position Difference: 19.97" and "Ghost Angle Difference: 10.1°". This informs the user that the real-time position and orientation of the sheath 110 (represented by the real-time image 432) is shifted by 19.97 units of distance (e.g., millimeters), and by 10.1 units of angular difference (degrees) from the desired or recorded position (represented by the ghost image 430). The display screen 420 provides a graphical user interface (GUI) 440 with arrow-keys to move the real-time image in an up direction (U), a down direction (D), a left direction (L), and a right direction (R). In FIG. 4B, the display screen 420 shows a GUI 441 which can provide interactive arrow-keys to allow the user to move the real-time position of the sheath 110 in a forward direction (F) and a backward direction (B), and/or arrow-keys to allow the user to move, rotate or twist the sheath distal tip in clockwise (CW) or counterclockwise (CCW) directions, until the difference measurements shown in screen section 442 meet a predetermined threshold.

The user, or the software system (based on the procedure plan), can set a threshold upon which the deviation (difference) between the non-real-time positon (ghost image) and the real-time image (real-time tool position) is deemed negligible so that a procedure can be safely completed. The threshold can be a percentage of difference in position and/or orientation of the real-time tool position with respect to the non-real-time (previously recorded) catheter position. For example the threshold can be set as a 100 difference between the recorded position of catheter tip with the camera and the real-time position of the catheter with the tool. The threshold can be adjusted according to the desired level of precision depending on the medical procedure to be performed.

The software can then indicate to the user when the deviation crosses this threshold. Since the comparison of the real-time tool position to the recorded, planned, or desired sheath position occurs during active insertion of the interventional tool through the sheath, the indication of correct alignment (or misalignment) could be set to occur only at the moment of crossing the threshold which can be from within to bigger than, and vice versa, or the period of deviation staying within the threshold. This indication can be, for example, an audible, visual, or haptic feedback in the form of an alert or notification provided to the user upon meeting the threshold. In one embodiment, a visual indication can be a change in visual appearance of the ghost image 430 and/or real-time image 432. The change in appearance can be a discrete switch in visual appearance once the threshold is crossed, or it can be a gradual change based on the amount of the deviation. Another possibility is to merge the visual properties of the ghost image 430 and real-time image 432. For example, if the ghost image 430 is yellow (a first color) and the real-time image 432 is blue (a second color), their intersected (overlapped) portions can turn green (a third color). In this manner, the user can be actively and clearly informed of a successful realignment between the desired or planned position and the real-time position. It is understood that, in referring to FIG. 4A and FIG. 4B, the term "position" refers to the position of the ghost image 430 with respect to position of real-time image 432 on the display screen 420. However, in terms of the steerable catheter sheath 110 and any interventional tool inserted through the sheath, the alignment refers to the "matching" of the recorded (non-real-time) coordinates with real-time coordinates of the position and orientation relationship between the distal tip of the sheath and the target site. In other words, while the display screen 420 may show a 2D position difference between the ghost image and the real-time image, a difference between the desired or recorded coordinates and the real-time coordinates of the sheath 110 with respect to the target site is considered in a 3D space. Hence, it is important that the software system can allow the user to observe the realignment in as many views as possible. FIG. 4A and FIG. 4B show top and side-view perspectives as an example, but other views including cross-sectional views will be available to the user.

Figure 5A:
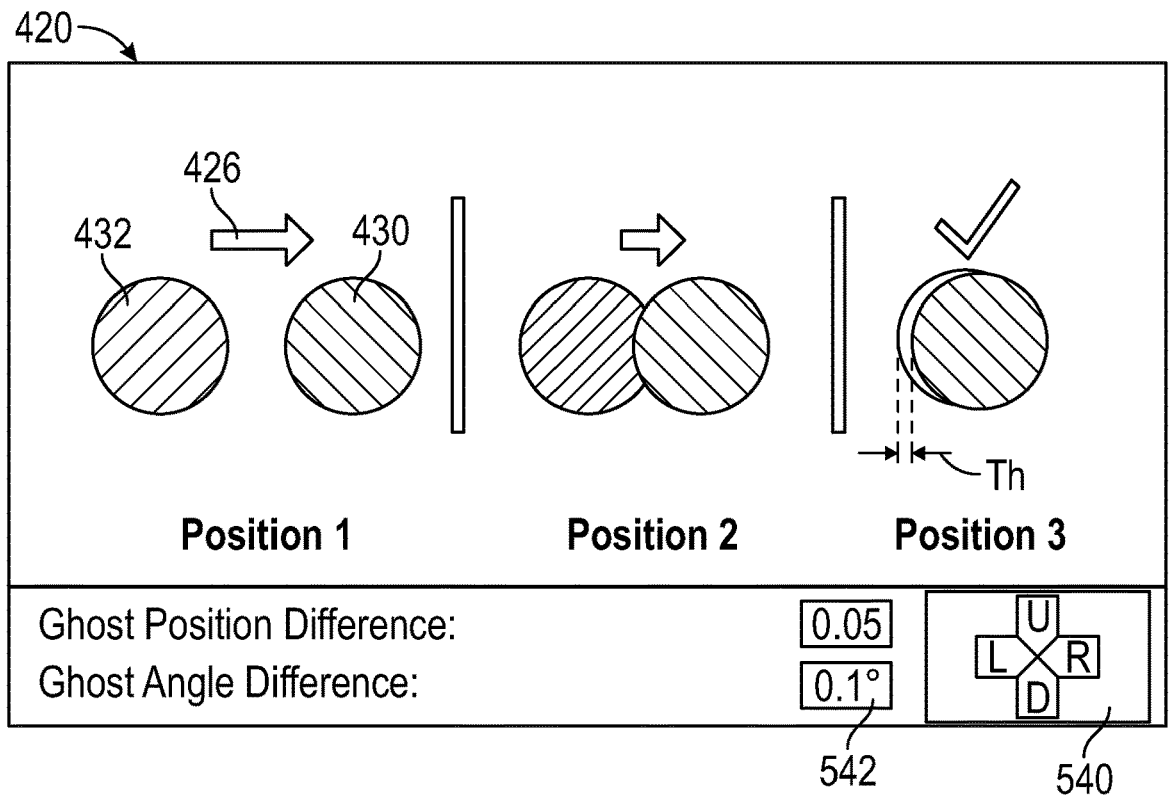
FIG. 5A shows an example of how the software system can indicate to the user when a difference between a positon of ghost image 430 and a position of real-time image 432 is within a certain threshold.

FIG. 5A shows an example of how the software system can indicate to the user when the difference between a ghost image 430 (recorded sheath position and/or orientation) and a real-time image 432 (real-time sheath position and/or orientation) is within a certain threshold. In the example shown in FIG. 5A, the display screen 420 shows a real-time image 432 (red circle) gradually changes from fully opaque to fully transparent as it approaches and overlaps the desired position of ghost image 430 (blue circle). In addition, the software system can cause the display screen to display an indicator 426 (e.g., an arrow) to inform the user which image should be realigned with the other. Display screen 420 may also provide specific information such as distance and angular difference between the ghost (non-real-time) image 430 and the real-time image 432. In this example, at Position 1, the indicator 426 shows a direction and a magnitude (represented by the size of the arrow) in which the real-time image 432 should be moved; at Position 2, the size of the arrow indicator 426 becomes smaller which is indicative that the distance between the two images is proportionally closer to each other; finally at Position 3, as the two images substantially overlap with each other to within a predetermined threshold (Th), the indicator becomes a verification marker (a checkmark) so the user can be informed that the alignment has been completed. At Position 3, in the case that the two images cannot be sufficiently overlapped within the threshold (Th), the verification marker can become an "X" shaped mark instead of a checkmark.

Similar to the previous embodiment, the display screen 420 provides a GUI 540 to allow the user to interactively move the real-time image 432 towards the ghost image 430. The GUI 540 is similar to GUI 440 shown in FIG. 4A. A display section 542 provides a measured positional and orientation difference between the real-time and ghost images based on the sheath position and orientation detected by the EM sensors or other similar tracking system. As the user moves the real-time image 432 towards the non-real-time ghost image 430, and thereby realigns the non-real-time position with the real-time position of the catheter sheath, the display section 542 shows that the measurements decrease to within a predetermined threshold, which can be about 1% to 10% of complete realignment.

Figure 5B:
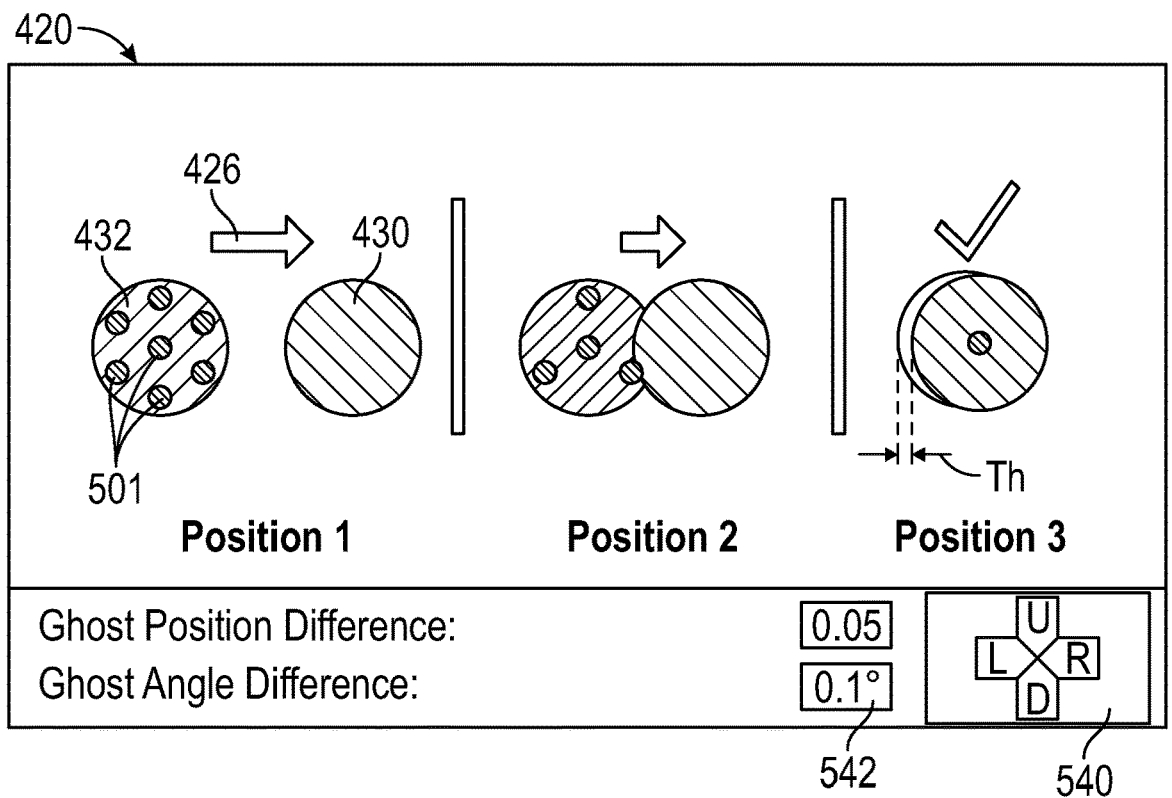
FIG. 5B shows an example of how the software system can indicate to the user when a difference in positon and orientation between a ghost image 430 and real-time image 432 is within a certain threshold.

FIG. 5B shows an example of how the software system can indicate to the user when a difference in positon and orientation between a ghost image 430 and real-time image 432 is within a certain threshold. According to FIG. 5B, the system can indicate to the user a difference in orientation between the ghost image 430 and the real-time image 432, by showing the angular difference in the format of texture represented by a plurality of dots 501. Here, a texture pattern like "dots" 501 on the real-time image 432 can represent angular difference in the orientation of the two images, and less dots represents less angular difference. Therefore, as the real-time image 432 becomes aligned with the ghost image 430, the number of dots 501 become less and less. Ultimately, it is important to align the real-time image with the non-real-time image such that both position and angle difference become as close to zero as possible to ensure that the interventional tool will be used in the intended target.

As mentioned elsewhere in this disclosure, the example shown in FIG. 5A and FIG. 5B illustrates a realignment to "match" both location and orientation of the real-time tool position (real-time image) and the recorded, desired, or planned sheath tip position (non-real-time ghost image). In FIG. 5A and FIG. 5B, the ghost and real-time images can be reversed such that the red circle (432) represents the non-real-time ghost image of the catheter sheath, and the blue circle (430) represents the real-time position (real-time image) of the sheath. In that case, the ghost image can gradually increase in transparency as the real-time position image approaches and overlaps the ghost image. This would also mean that the arrows (indicator 426) would point in the opposite direction (right to left in the figure), and the blue circle would move from right to left until it overlaps the red circle. Moreover, as long as the software system provides a clear indication for realigning the real-time position with the non-real-time position of the catheter sheath, the shape of the ghost image and real-time mage is not limited to a circle; the same applies to the use of color or transparency of the images. However, regardless of the form in which the non-real-time ghost image 430 and the real-time image 432 are represented, the alignment steps would still occur substantially as outlined in the workflow of FIG. 3.

The software can also assist the user in aligning the real-time position with the ghost position through other instructions and/or certain image perspectives. One way the software system can guide the user is by having arrows showing the direction the user should bend each section of the catheter sheath 110. An optimal way of presenting these arrows is in the first person view (FPV). For example, in one embodiment, the system can show arrows corresponding to the control joystick direction of the gamepad controller. In another embodiment, the arrows can be presented by showing a combination of top/side/front views so the user can visually know how much displacement exists in all directions. FIG. 4A, FIG. 4B, and FIG. 5A—FIG. 5B show some examples of how the software system can display indications for tool displacement so that the user can realign the real-time position image 432 with the non-real-time ghost image 430. In must be noted that the angle values shown in the display section 442 of FIG. 4B and display section 542 of FIG. 5A-5B may not necessarily refer to a clockwise/counter-clockwise movement of the catheter. Instead, these values can refer to the yaw/pitch angle (combined value) of the distal tip of the catheter. However, in at least some embodiments, a roll value of the catheter can also be provided (which could then be expressed as CW/CCW values).

Figure 6A:
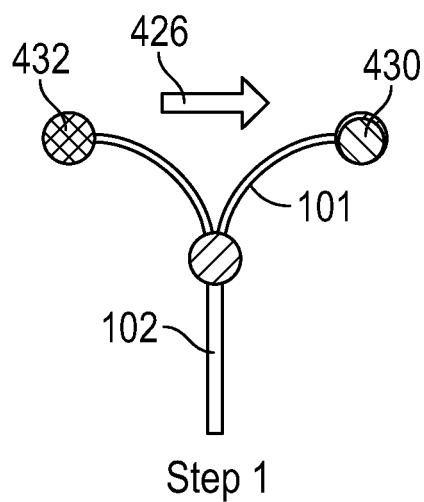
FIG. 6A and FIG. 6B is an example of how the software system can assist the user in correcting deviations of the steerable sheath in a specific order.
Figure 6B:
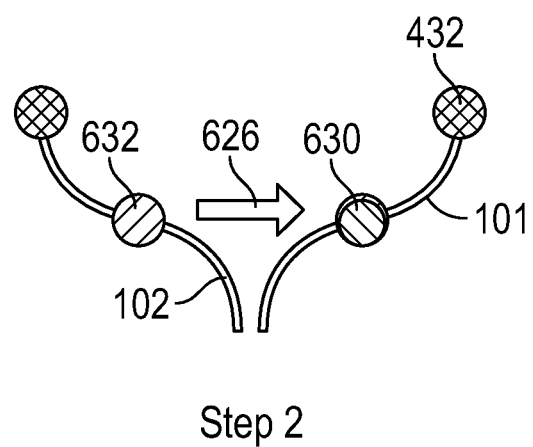

Since the alignment deviation (misalignment) between the real-time position and desired ghost position of the steerable catheter sheath 110 can occur in both position and orientation parameters, the software system can be programmed to assist the user in correcting these deviations in a specific order. FIG. 6A and FIG. 6B illustrate an example of how the software system can assist the user in correcting deviations in a specific order. In FIG. 6A and FIG. 6B, the software system displays the end of each steerable section represented by a circle of a different color. The distal end of the distal section 101 (the tip of the sheath) is displayed as a circle of a first color (green) and the distal end of the middle section 102 is displayed as a circle of a second color (red). Additional sections, or additional inflection points between different sections, can be displayed in other colors, sizes, or representations. In a multi-section catheter sheath 110, for example, as shown in FIG. 2B, the steerable sections are joined by linking joints 104, and each section can be controlled separately. In such multi-section catheter sheath, actuating the distal section 101 affects both the position and orientation of the tip of the sheath, while bending the middle section 102 affects mostly the position (location) of the tip. Therefore, according to at least one embodiment, it can be more efficient for the system to direct the user to first align the orientation of the tip by controlling the distal section, and then align the position of the tip by controlling the middle section.

FIG. 6A shows an example where the software system displays an indicator 426 (an arrow in a first direction from left to right) to inform the user this is a first step (STEP 1) for realigning the position and orientation of a real-time image 432 (green circle) with the position and orientation of a ghost image 430 (blue circle) of the tip of distal section 101. In this case, the user can drag the real-time image 432 (green circle) towards the ghost image 430 (blue circle) until the two images overlap. FIG. 6B shows an example where the software system displays an arrow indicator 626 to inform the user this is a second step (STEP 2) for realigning only the position of a real-time image 632 (red circle) with the position of a ghost image 630 (blue circle) of the middle section 102. When the alignment steps are to be performed in a predetermined or preferred order, the software system may not allow the alignment steps to be performed out of the predefined order. That is to say, the software can be programmed to allow alignment of the middle section 102 only after the position and orientation of the distal section 101 has been completed. However, depending on how the software system is programmed, the opposite can also be true, i.e., the software can be programmed to allow alignment of the middle section 102 before the position and orientation of the distal section 101 is completed.

In other words, it is not impossible for the distal section (tip) and middle section of the catheter sheath to be correctly re-aligned out of the pre-defined order. In some embodiments, the order in which one section gets controlled first may not be relevant. In fact, both sections can both be controlled simultaneously. But the software must convey to the user that each section will need to have their own bending amount/direction to reach a desired realignment, so for workflow purposes it might be easiest to direct the user to perform realignment by controlling one section at a time, while observing the real-time feedback in the display screen of the system.

Figure 7A:
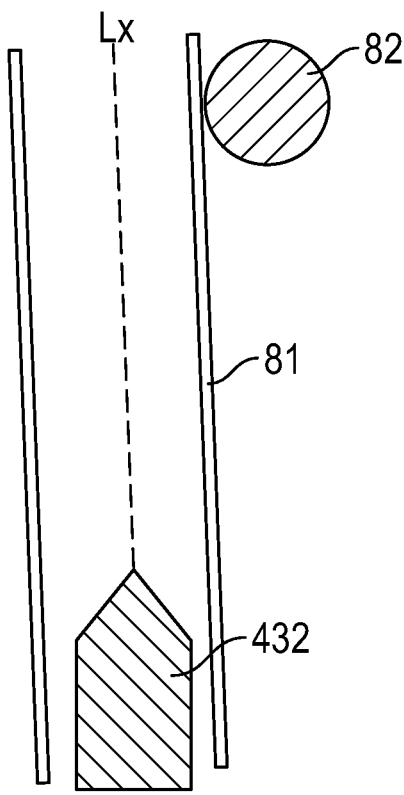
FIGS. 7A and 7B shows another example of how the software system can indicate to the user a difference in position and/or orientation between a ghost image 430 and a real-time image 432 with respect to one or more target site(s) 82.
Figure 7B:
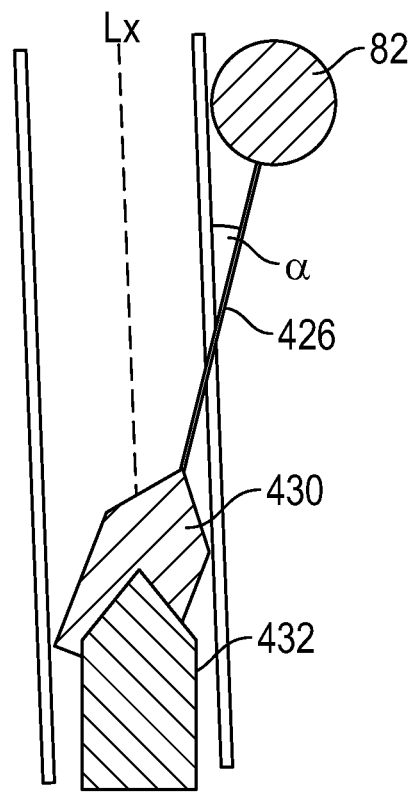

FIGS. 7A and 7B shows another example of how the software system can indicate to the user the difference in position and/or orientation between a ghost image 430 and a real-time position image 432 with respect to one or more target site(s) 82. FIG. 7A is meant to show the real-time position of the sheath 110 represented by a real-time image 432 (in dark blue). FIG. 7B adds the proposed/desired/ideal ghost position represented by ghost image 430 (light blue), presented here as a simplified model which takes into consideration the catheter dimension and lumen size, though more factors need to be included such as EM sensor position, kinematics limitations, etc. This shows how the ideal position should stay along the centerline (Lx) and within the bounds of the lumen 81, and should minimize the distance 426 to the target site 82. The ghost image 430 can get closer to the target site 82 by moving further along the path, but the angle (a) of the catheter would cause the catheter to collide with the wall of the lumen 81.

<Recording and Displaying Multiple Ghost Images>

Figure 8:
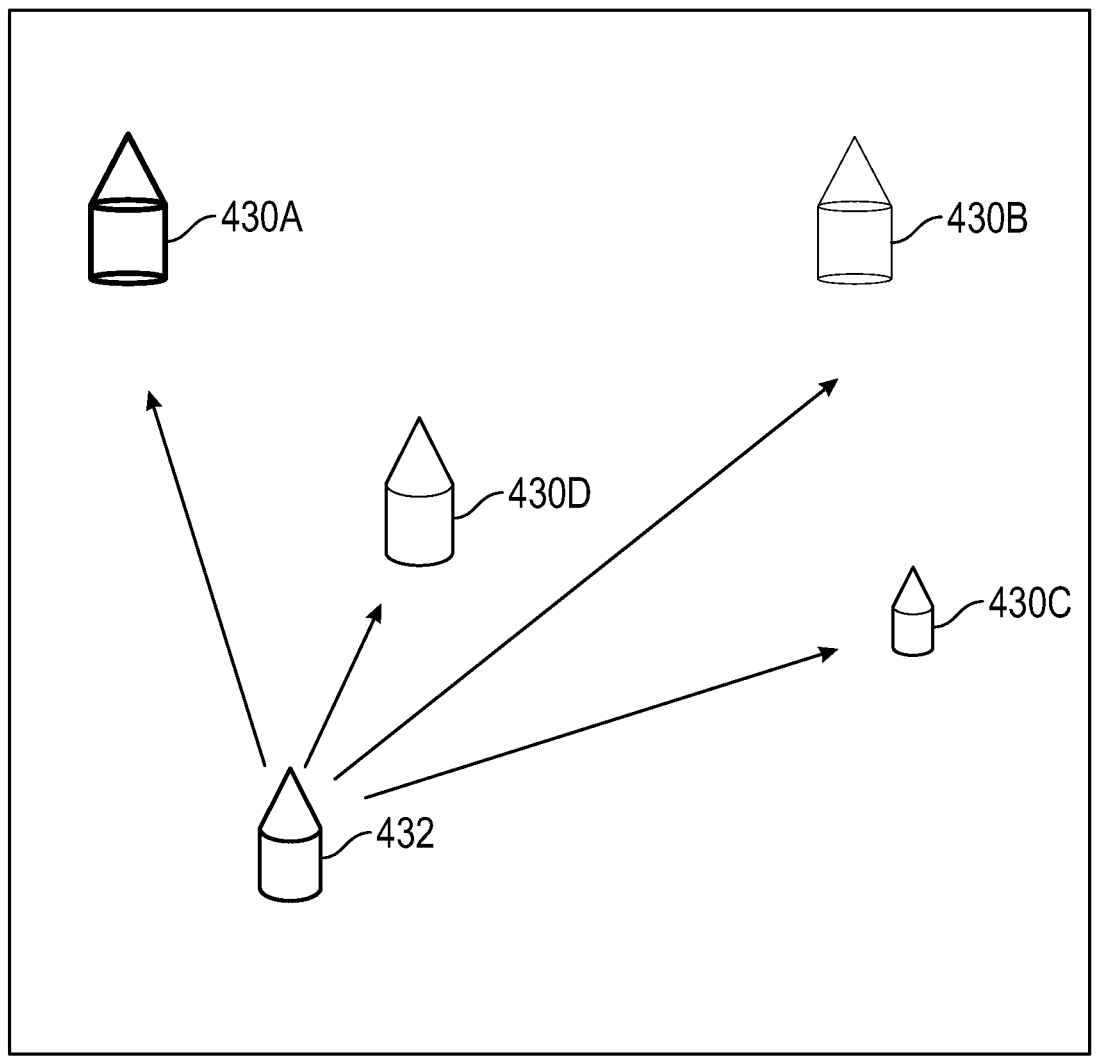
FIG. 8 illustrates an example of how the software system can display differences between a real-time sheath position represented by a real-time image 432 and multiple non-real-time (recorded or planned) sheath positions represented by multiple ghost images 430.

FIG. 8 illustrates an example of displaying multiple ghost positions and a real-time position simultaneously in a display screen 420. Multiple recorded or planned ghost positions of the sheath tip are displayed as a ghost image 1 (430A), ghost image 2 (430B), ghost image 3 (430C), and a ghost image 4 (430D). The system also displays a "real-time" sheath position, as a real-time image 432. Clockwise from the top left of FIG. 8, the ghost images are distinguished from each other and from the real-time mage 432, as follows: ghost image 430A is shown as a wireframe image, ghost image 430B is shown as transparent image, ghost image 430C is shown in different size, and ghost image 430D is shown in different color from the real-time image 432.

According to at least one embodiment, the user can create as many recorded positions as necessary, and each can be provided as a ghost position with a unique annotation (ID), name, color, shape, etc. The user can also selectively hide or show each recorded ghost position as desired. Moreover, the system can allow the user to select or designate which one multiple ghost positions (which ghost image) remains "active" for the aforementioned realignment procedure. Active or inactive ghost images can be automatically designated by the system software, for example, by determining which ghost image positon meets a desired threshold indication for realignment.

According to one embodiment, after having removed the imaging device from the steerable catheter sheath 110 and when the actual interventional tool is being advanced through the sheath towards the target site, the system can provide virtual views using the recorded position, rather than the real-time position, if the user chooses to do so. For example, if one of the recorded positions was aiming at a specific part of the airway earlier in the procedure, the user can swap to the virtual first-person camera view at the recorded position/orientation to recall what was being inspected. A virtual first person camera view is placed at the tip of the EM-tracked catheter sheath within the 3D anatomical model, and this camera view should match the recorded endoscopic view obtained when the imaging device was first used. The virtual first-person view can be shown in real-time (using the real-time EM position), and should ideally match the real-time endoscope image. In the embodiment of a system having this first-person view correspond to a ghost position, the first-person view will match the endoscope view at same point in time when the ghost was created.

The use of multiple ghost images can be advantageous in a use case scenario where the clinician is performing multiple biopsies. In this scenario, the user can record the position of the catheter sheath during each biopsy sample, or the software system can be programmed to automatically record the position for each biopsy sample. This can help the clinician ensure that the next sample is a safe distance away from a prior attempt, and not overlapping a previously sampled region. The user can also label each real sample with the corresponding name/id of the recorded positions, for potential future reference. This can be useful, for example, after pathology to note where in the lesion the cancer was found.

In addition, the software system can be programmed to create multiple ideal ghost images for multiple biopsy samples, and these ghost images can be arranged to ensure there is no overlap in the samples. In this case, the software can automatically change the 'active' ghost after each sample, as well as automatically show/hide the ghosts accordingly.

<Serial Recording of Ghost Positions>

In some embodiments, the software system can also capture a series of catheter positions along the insertion path of the catheter sheath. The positions along the insertion path of the catheter sheath can be captured by the endoscope camera and/or by the one or more EM sensors arranged on the sheath. The interval of these captures can be adjustable at the user's convenience. For example, the position of the catheter can be recorded every predetermined amount of time (every few of seconds, e.g., every 1 second) during the navigation sequence. The appearance of all ghost positions in this series can be modified collectively, or individually. The user can also display al ghost images all at once, or can selectively show or hide them individually. Using the above example, the user can show all of the recording at once to visualize the path that was followed by the tip of the catheter to arrive to the target site.

The software can also cycle through each position in the series, at the interval they were recorded or at any desired interval. Again using the above example, the user would see an animation of the catheter traveling down the insertion path. The software can apply the ghost image positions to the virtual camera views as the playback cycles through each position in the series. Using the same example, the user would then see a recreation of the insertion trajectory through the virtual first-person camera view. Alternatively, in the case where the catheter sheath was initially navigated using an endoscope camera, the user can see the playback of the actual endoscope camera recording. Furthermore, the system can be programmed to display (replay) the virtual path and the recorded endoscope view.

The software can also set each recorded position as "active" for realignment as the software cycles through the series during playback. Using the playback, the user will able to see the deviation measurements change throughout the cycle. One use case scenario of serial recording of ghost positions is to assist the clinician in navigation/targeting throughout the respiratory cycle of a patient. If, for example, the clinician recorded the position of the catheter tip when the lesion was aligned using the camera at a particular respiratory phase, it is possible that the lesion moves out of alignment at other respiratory phases. Comparing the real-time position to a recorded position can help the clinician identify where the patient is in the respiratory cycle, and the clinician can know that when the real-time and saved positions are re-aligned, then the lesion will be aligned with the trajectory at the corresponding respiratory phase. The tracking of the real-time position can also show the full range of motion of the respiratory cycle, and, if the camera is still in the catheter, it can reveal to the clinician at what points the lesion is or is not aligned with the trajectory.

Figure 9A:
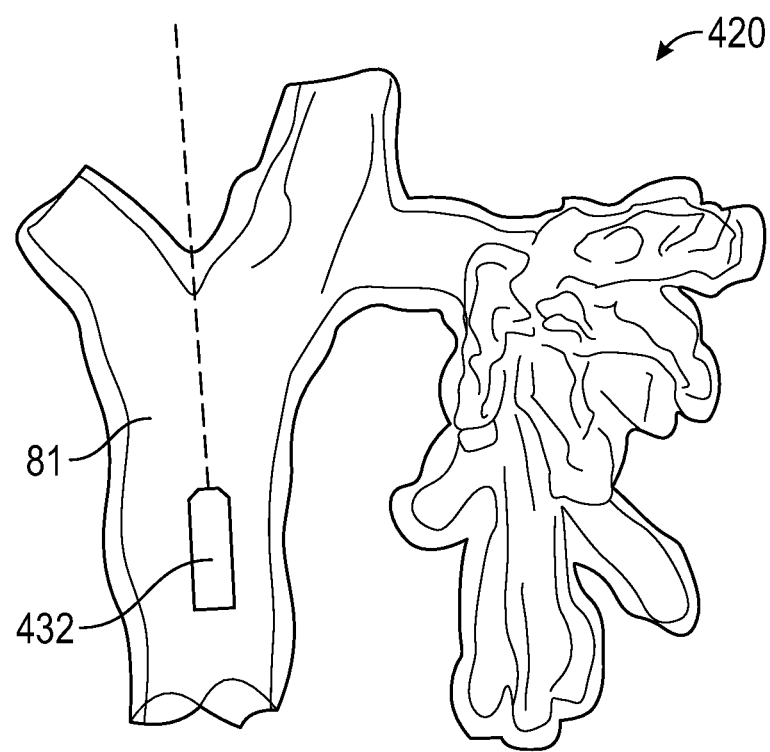
FIG. 9A and FIG. 9B show an example embodiment where the system is configured to provide a virtual first-person camera view to align the real-time catheter position with a pre-recorded or planned ghost position.
Figure 9B:
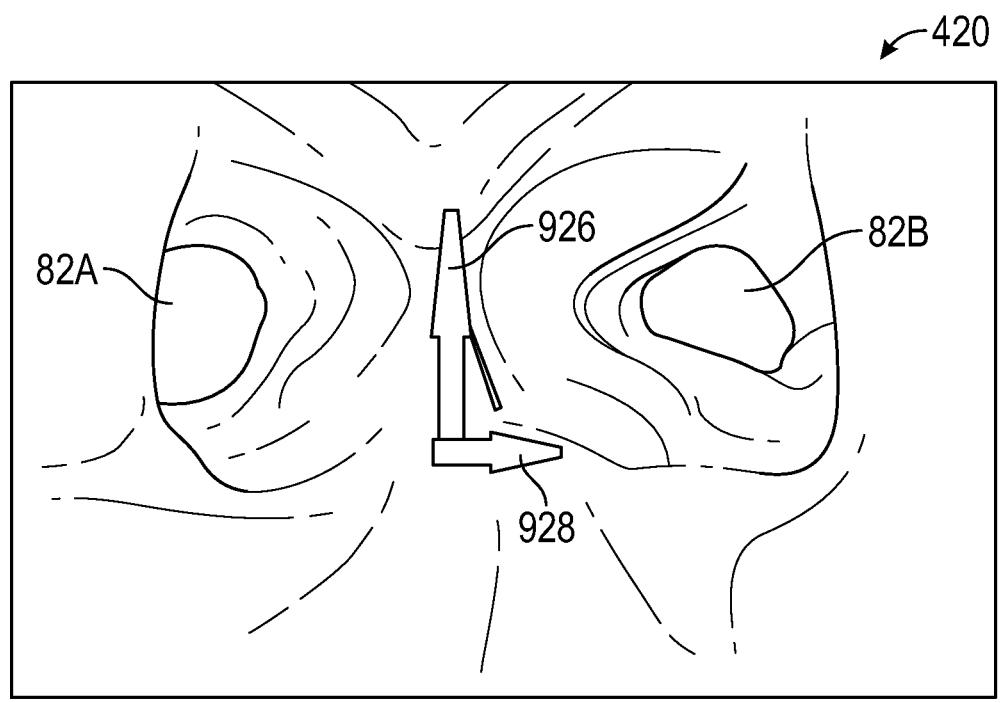

FIG. 9A and FIG. 9B show an example embodiment where the system is configured to provide a virtual first-person camera view to align the real-time catheter position with a pre-recorded or planned ghost position. FIG. 9A shows the display screen 420 displaying a top view of a virtual real-time image 432 advancing through a lumen 81 (e.g., an airway of a patient) towards a target (e.g. the first carina). FIG. 9B shows the display screen 420 displaying a first-person view (FPV) of a camera located at the distal tip of the catheter sheath. The user must align and direct the distal tip of the catheter sheath towards one bifurcation of the first carina. To that end, arrow indicators 926 and 928 can be used to assist the user in re-aligning the real-time position with the ghost position (planned or pre-recorded position). It is understood that the displayed FPV does not have to be only a virtual image; it can also be an overlay of the ghost image over the actual endoscope image. In FIG. 9B, the arrow indicators 926 and 928 in the FPV can inform the user of the direction to bend the catheter sections (which also corresponds to the direction to press the joystick controller). There can be a different arrow for each controllable section. In this example, the upright arrow 926 (Red) can be for controlling the tip, and the horizontal arrow 928 (Green) can be for controlling the middle section of the catheter sheath. The arrows 926 and 928 can change based on the distance to the ghost image. For example, the direction the arrow will change as the catheter point of view with the desired target (ghost image), and the magnitude (size) of the arrow can reflect the distance to the correct alignment. In that case, the closer the real-time position of the catheter or tool gets to the ghost image, the shorter the arrow will become, until it disappears when the alignment is within a desired threshold. In FIG. 9B, the ghost image (or desired target) can be represented by one of the carina bifurcations (i.e., a target 82A or target 82B).

Figure 10:
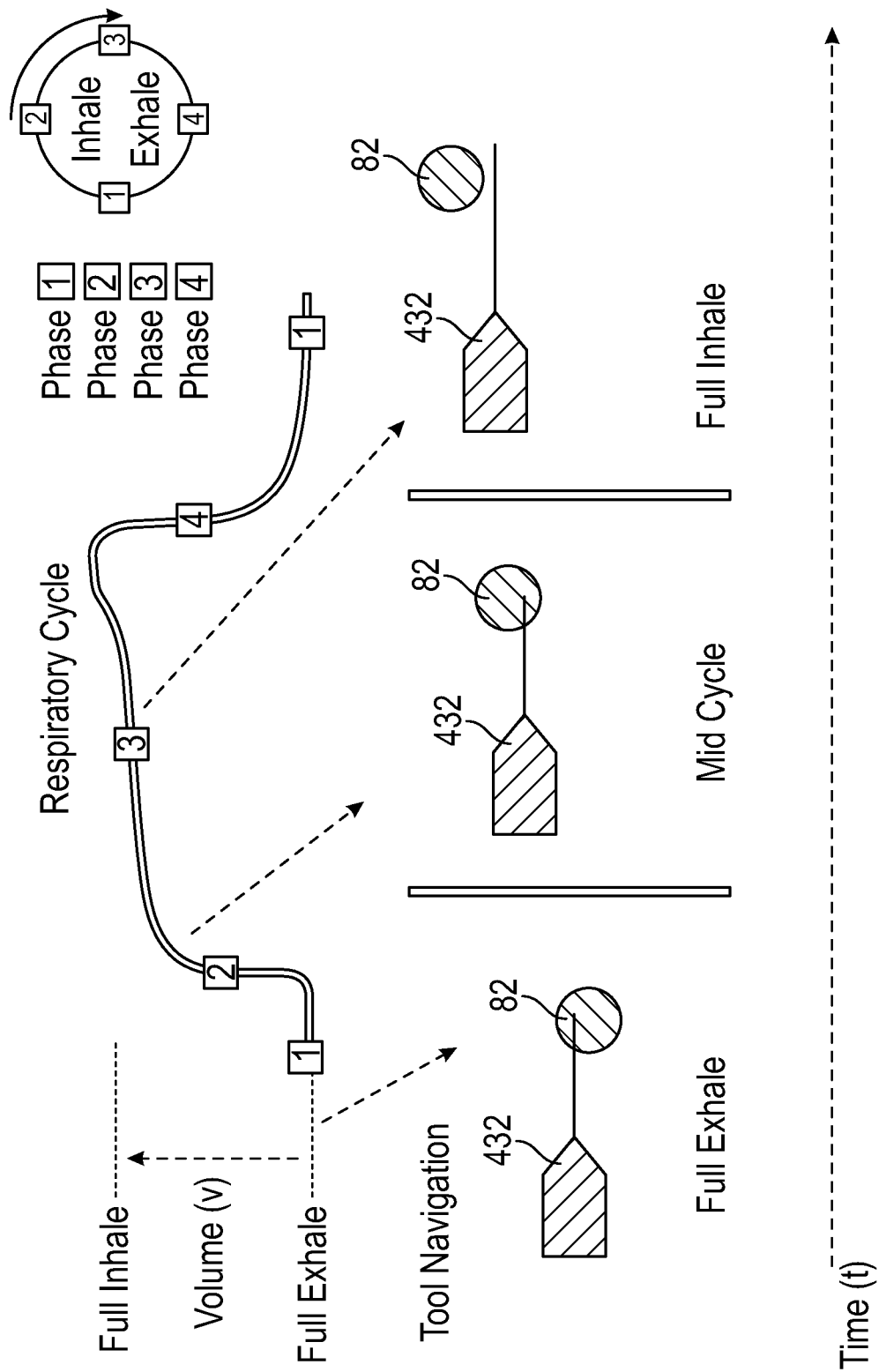
FIG. 10 shows an example embodiment where the system is configured to record cyclic motion waveforms corresponding to a physiological activity of the patient, and the processor outputs to a display screen the non-real time insertion trajectory and the real-time insertion trajectory associated with a difference in motion phase within one or more cycles of the cyclic motion waveforms.

FIG. 10 shows an example embodiment where the system is configured to record cyclic motion waveforms corresponding to a physiological activity of the patient, and the processor outputs to a display screen the non-real time insertion trajectory and the real-time insertion trajectory associated with different motion phases within one or more cycles of the cyclic motion waveforms. According to FIG. 10, the processor of the system is programmed to further output to the display screen navigation guidance data to inform the user how to manipulate the distal section of the sheath along the real-time insertion trajectory such that the real-time insertion trajectory becomes aligned with the target at a desired motion phase.

More specifically, FIG. 10 shows that the real-time image 432 of the catheter is aligned with the target 82 at Full Exhalation and Mid-Cycle, but it does not align with the target 82 at Full Inhalation. One way to determine this is to have the camera in the catheter during one or more cycles (respiration cycles), and visually observe if the distal tip of the catheter sheath is aligned with the lesion (target 82). Then, using this knowledge (which can be prerecorded), the software system can detect the phase of the respiratory cycle by detecting what ghost image the real-time catheter is nearest to. If the real-time image of the catheter is nearest to a ghost image that is known to be misaligned, for example the Full Inhalation position, in FIG. 10, then the software can alert the physician to not take the sample until the real-time position of the catheter returns nearer to a position that is correctly aligned. For example, in FIG. 10, the ghost image 432 at Full Exhale and at Mid Cycle phases would be considered correctly aligned with the target 82. Therefore, since the biologic cyclic motion waveforms are known to be substantially uniform for a given subject (patient), it would be advantageous to record at least one cycle of the biological cyclic motion waveform and correlate that waveform with the ghost image data to display navigation guidance data to inform the user how to manipulate one or more sections of the sheath along the real-time insertion trajectory such that the real-time insertion trajectory becomes aligned with the target at a desired motion phase.

Software Related Disclosure

Embodiment(s) of the present disclosure can be realized by computer system 400 or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer system may comprise one or more processors (e.g., central processing unit (CPU) 410, micro processing unit (MPU)) and may include a network of separate computers or separate processors to read out and execute the computer executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Other Embodiments, Modifications, and/or Advantages

The various embodiments disclosed herein describe systems, methods, and computer-readable media of providing endoscope navigation guidance for controlling a catheter sheath having a proximal section attachable to an actuator and a distal section insertable into a lumen of a patient. The sheath can be advantageously controlled to be inserted through a lumen and maintained in a positional relation with respect to a target site. The sheath can operate with different configurations without removing it.

Specifically, a processor is in operative communication with an EM sensor system and with the actuator to provide navigation guidance to a user that inserts the sheath through the lumen. The processor is programmed to: generate a ghost image based on first data about a non-real-time insertion trajectory for inserting the sheath through the lumen and aligning the distal section of the sheath with the target site; generate a real-time image based on second data about a real-time insertion trajectory for inserting an interventional tool through the tool channel of the sheath towards the target site, the second data acquired by the EM sensor system while guiding the interventional tool through the sheath and guiding the distal section of the sheath towards the target site. A display screen displays information for the user to manipulate the distal section of the sheath towards the target site such that the real-time image overlaps with at least part the ghost image and the real-time insertion trajectory becomes aligned with the non-real-time insertion trajectory.

The ghost position and difference between real-time and ghost images is determined by forward kinematics based on positional information provided by the EM sensors. An endoscope imaging device (the endoscopic camera) is not necessarily considered as "a tool" per se, as its role in the tool exchange change is to give the user guidance.

The ghost image, when presented at a proposed/desired/ideal position, it can save the effort to attempt maneuvering the catheter distal end prior to the biopsy tool exchange as it may be challenging to reach the proposed position, however it can be possible due to the change of overall characteristics of the sheath such as rigidity and flexibility with the biopsy tool.

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. For example, the present disclosure has been described above in terms of exemplary embodiments. However, there are many variations not specifically described to which the present disclosure could be applicable. For example, while the various embodiments are described with respect to an endoscope for use in medical procedures, the disclosure would be also applicable with respect to mechanical procedures of a borescope for use within various mechanical structures. Therefore, the scope of the following claims is to be accorded the broadest interpretation so as to encompass all such modifications and equivalent structures and functions.

What is claimed is:
1. A system comprising:
 a sheath having a proximal section attachable to an actuator and a distal section insertable into a lumen of a patient, the sheath having a tool channel and configured to receive an actuating force from the actuator to navigate the distal section of the sheath through the lumen and towards a target site;

a sensor system configured to detect a positional relation of the distal section of the sheath with respect to the target site; and a processor in operative communication with the sensor system and the actuator, wherein the processor is configured to:

generate a ghost image of the sheath based on first data about at least part of a non-real-time insertion trajectory of the sheath inserted through the lumen and aligned with the target site, generate a real-time image of the sheath based on second data about at least part of a real-time insertion trajectory of an interventional tool inserted through the tool channel of the sheath towards the target site, the second data acquired by the sensor system while the interventional tool is inserted through the sheath, and output navigation guidance data to a display screen for informing the user how to manipulate the distal section of the sheath such that the display screen displays the real-time image of the sheath overlaps with at least part of the ghost image of the sheath and the real-time insertion trajectory becomes aligned with the non-real-time insertion trajectory.

2. The system according to claim 1, wherein the non-real-time insertion trajectory is a recorded insertion trajectory acquired by an imaging device arranged in the tool channel of the sheath and inserted into the lumen prior to inserting the interventional tool, and wherein the first data about the non-real-time insertion trajectory includes image data corresponding to a series of images acquired by the imaging device along the lumen when the distal section of the sheath is inserted through the lumen and the imaging device is aligned with the target site.

3. The system according to claim 2, wherein the processor is further configured to prompt the user to remove the imaging device from the sheath without removing the sheath from the lumen, and prompt the user to insert the interventional tool along the tool channel of the sheath, wherein the real-time insertion trajectory is an insertion trajectory recorded by one or more sensors of the sensor system when the interventional tool is inserted into the tool channel of the sheath, and wherein the second data about the real-time insertion trajectory includes a position and/or orientation of the distal section of the sheath acquired by the sensor system when the interventional tool is inserted into the sheath and the distal section of the sheath is aligned with the target site.

4. The system according to claim 2, wherein the interventional tool is a surgical tool selected from a group consisting of: clamps, graspers, scissors, staplers, or ablation needles, and wherein the processor outputs onto a display screen the ghost image of the sheath and the real-time image of the sheath along with a difference between a non-real-time position and/or orientation of the distal section of the sheath without the surgical tool and a real-time position and/or orientation of the distal section of the sheath with the surgical tool arranged in the tool channel therein.

5. The system according to claim 1, wherein the non-real-time insertion trajectory is a planned insertion trajectory based on pre-operative imaging of the patient, and wherein the processor outputs onto a display screen the ghost image of the sheath and the real-time image of the sheath along with a difference between one or more points along the planned insertion trajectory and one or more points along the real-time insertion trajectory.

6. The system according to claim 1, wherein the processor is further configured to record cyclic motion waveforms corresponding to a physiological activity of the patient, wherein the processor outputs to a display screen the non-real time insertion trajectory and the real-time insertion trajectory associated with different motion phases within one or more cycles of the cyclic motion waveforms, and wherein the processor further outputs to the display screen the navigation guidance data to inform the user how to manipulate the distal section of the sheath along the real-time insertion trajectory such that the real-time insertion trajectory becomes aligned with the non-real-time insertion trajectory at a desired motion phase within a cycle of physiological motion.

7. The system according to claim 1, wherein the processor outputs to a display screen the navigation guidance data as one or more arrow images for informing the user how to move the real-time image of the sheath towards the ghost image of the sheath, and wherein the processor further outputs to the display screen an indication of when the real-time image of the sheath moves within a threshold distance from the ghost image of the sheath.

8. The system according to claim 1, wherein the processor outputs to a display screen the ghost image of the sheath and the real-time image of the sheath such that an appearance of the ghost image of the sheath is different from the real-time image of the sheath in one or more of identification, size, shape, color, or opacity so the user can visually distinguish the ghost image of the sheath from the real-time image of the sheath when both images are displayed simultaneously.

9. The system according to claim 1, wherein the processor outputs to a display screen the ghost image of the sheath represented by a series of images recorded by the endoscope imaging device along the non-real-time insertion trajectory, and wherein the display screen shows all of the recorded series of images at once to visualize a path that was followed by the sheath.

10. The system according to claim 9, wherein the processor outputs to the display screen the path followed by the sheath through the lumen as a recreation of a virtual first-person camera view.

11. A method of providing endoscope navigation guidance for controlling a sheath having a proximal section attachable to an actuator and a distal section insertable into a lumen of a patient, the method comprising:

transmitting an actuating force from the actuator to the sheath to navigate the distal section of the sheath through the lumen and towards a target site;

detecting, via a sensor system, a positional relation of the distal section of the sheath with respect to the target site, processing data, using a processor in operative communication with the sensor system and the actuator, to provide navigation guidance to a user that inserts the sheath through the lumen, the data processing comprising:

generating a ghost image of the sheath based on first data about at least part of a non-real-time insertion trajectory of the sheath inserted through the lumen towards the target site, generating a real-time image of the sheath based on second data about at least part of a real-time insertion trajectory of an interventional tool inserted through the tool channel of the sheath towards the target site, the second data acquired by the sensor system while the interventional tool is inserted through the sheath towards the target site, and outputting navigation guidance data to a display screen for informing a user how to manipulate the distal section of the sheath such that the display screen displays the real-time image of the sheath overlaps with at least part of the ghost image of the sheath and the real-time of the sheath insertion trajectory becomes aligned with the non-real-time insertion trajectory.

12. The method according to claim 11, further comprising:

recording, using the processor, an insertion trajectory of the sheath, wherein the non-real-time insertion trajectory is the recorded insertion trajectory of the sheath acquired by an imaging device arranged in the tool channel of the sheath and inserted into the lumen prior to inserting the interventional tool, and wherein the first data about the non-real-time insertion trajectory includes image data corresponding to a series of images acquired by the imaging device along the lumen when the distal section of the sheath is inserted through the lumen and the imaging device is aligned with the target site.

13. The method according to claim 12, further comprising:

prompting the user to remove the imaging device from the sheath without removing the sheath from the lumen, and prompting the user to insert the interventional tool along the tool channel of the sheath, wherein the real-time insertion trajectory is an insertion trajectory recorded by one or more sensors of the sensor system when the interventional tool is inserted into the tool channel of the sheath, and wherein the second data about the real-time insertion trajectory includes a position and/or orientation of the distal section of the sheath acquired by the sensor system when the interventional tool is inserted into the sheath and the distal section of the sheath is aligned with the target site.

14. The method according to claim 12, wherein the interventional tool is a surgical tool selected from a group consisting of: clamps, graspers, scissors, staplers, or ablation needles, and wherein the processor outputs onto a display screen the ghost image of the sheath and the real-time image of the sheath along with a difference between a non-real-time position and/or orientation of the distal section of the sheath without the surgical tool and a real-time position and/or orientation of the distal section of the sheath with the surgical tool arranged in the tool channel therein.

15. The method according to claim 11, wherein the non-real-time insertion trajectory is a planned insertion trajectory based on pre-operative imaging of the patient, and wherein the processor outputs onto a display screen the ghost image of the sheath and the real-time image of the sheath along with a difference between one or more points along the planned insertion trajectory and one or more points along the real-time insertion trajectory.

16. The method according to claim 11, wherein the processor is further configured to record cyclic motion waveforms corresponding to a physiological activity of the patient, wherein the processor outputs to a display screen the non-real time insertion trajectory and the real-time insertion trajectory associated with different motion phases within one or more cycles of the cyclic motion waveforms, and wherein the processor further outputs to the display screen the navigation guidance data to inform the user how to manipulate the distal section of the sheath along the real-time insertion trajectory such that the real-time insertion trajectory becomes aligned with the non-real-time insertion trajectory at a desired motion phase within a cycle of physiological motion.

17. The method according to claim 11, wherein the processor outputs to a display screen the navigation guidance data as one or more arrow images for informing the user how to move the real-time image of the sheath towards the ghost image of the sheath, and wherein the processor further outputs to the display screen an indication of when the real-time image of the sheath moves within a threshold distance from the ghost image of the sheath.

18. The method according to claim 11, wherein the processor outputs to a display screen the ghost image of the sheath and the real-time image of the sheath such that an appearance of the ghost image of the sheath is different from the real-time image of the sheath in one or more of identification, size, shape, color, or opacity so the user can visually distinguish the ghost image of the sheath from the real-time image of the sheath when both images are displayed simultaneously.

19. The method according to claim 11, wherein the processor outputs to a display screen the ghost image of the sheath represented by a series of images recorded by the endoscope imaging device along the non-real-time insertion trajectory, and wherein the display screen shows all of the recorded series of images at once to visualize a path that was followed by the sheath.

20. The method according to claim 19, wherein the processor outputs to the display screen the path followed by the sheath through the lumen as a recreation of a virtual first-person camera view.

21. A non-transitory computer-readable medium configured to store computer-executable instructions for implementing the method of providing endoscope navigation guidance, according to claim 11.

* * * * *